(12) United States Patent
Sudlow et al.

(10) Patent No.: US 11,511,057 B2
(45) Date of Patent: Nov. 29, 2022

(54) AEROSOL DELIVERY SYSTEM

(71) Applicant: Nerudia Limited, Liverpool (GB)

(72) Inventors: Tom Sudlow, Liverpool (GB); Chris Lord, Liverpool (GB); David Jones, Liverpool (GB); Edward Ross Shenton, Liverpool (GB)

(73) Assignee: NERUDIA LIMITED, Liverpool (GB)

( * ) Notice: Subject to any disclaimer, the term of this patent is extended or adjusted under 35 U.S.C. 154(b) by 599 days.

(21) Appl. No.: 16/608,743

(22) PCT Filed: Apr. 24, 2018

(86) PCT No.: PCT/EP2018/060503
§ 371 (c)(1),
(2) Date: Oct. 25, 2019

(87) PCT Pub. No.: WO2018/197514
PCT Pub. Date: Nov. 1, 2018

(65) Prior Publication Data
US 2021/0093804 A1  Apr. 1, 2021

(30) Foreign Application Priority Data
Apr. 25, 2017 (GB) .................................... 1706593

(51) Int. Cl.
*A61M 15/06* (2006.01)
*A24F 40/48* (2020.01)
(Continued)

(52) U.S. Cl.
CPC ............. *A61M 15/06* (2013.01); *A24F 40/42* (2020.01); *A24F 40/44* (2020.01); *A24F 40/46* (2020.01);
(Continued)

(58) Field of Classification Search
CPC .. A61M 15/06; A61M 11/042; A61M 15/009; A61M 2205/0233; A24F 40/48;
(Continued)

(56) References Cited

U.S. PATENT DOCUMENTS

| 5,766,709 A | 6/1998 | Geddes et al. |
| 8,997,754 B2* | 4/2015 | Tucker ..................... H05B 3/44 |
| | | 131/273 |

(Continued)

FOREIGN PATENT DOCUMENTS

| CN | 103876289 A | 6/2014 |
| CN | 203662018 U | 6/2014 |

(Continued)

OTHER PUBLICATIONS

Office Action for Chinese Application No. 201880039520.X dated Aug. 11, 2021 (12 pages).

(Continued)

*Primary Examiner* — Abdullah A Riyami
*Assistant Examiner* — Vladimir Imas
(74) *Attorney, Agent, or Firm* — J. Miguel Hernandez; James R. Gourley; Carstens, Allen & Gourley, LLP

(57) ABSTRACT

An aerosol-delivery system having: an aerosol-generation apparatus with a receptacle for receiving a carrier; a heater; and a carrier for an aerosol precursor with a housing for location in said receptacle. Said housing is configured to provide a fluid pathway between a first end that is disposed in fluid engagement with an inlet of said aerosol-generating apparatus and a second end that is disposed in fluid engagement with an outlet of said aerosol-generating apparatus. A fluid-transfer article is located within said housing, the fluid-transfer article having a first region for holding an aerosol precursor and for transferring said aerosol precursor to an activation surface of a second region of said article, (Continued)

said activation surface disposed at an end of said carrier configured for thermal interaction with a heater of said aerosol-generation apparatus.

27 Claims, 12 Drawing Sheets

(51) Int. Cl.

| | |
|---|---|
| *A24F 40/44* | (2020.01) |
| *A24F 40/42* | (2020.01) |
| *A61M 11/04* | (2006.01) |
| *A61M 15/00* | (2006.01) |
| *A24F 40/46* | (2020.01) |
| *H05B 3/20* | (2006.01) |
| *A24F 40/10* | (2020.01) |

(52) U.S. Cl.

CPC .......... *A24F 40/48* (2020.01); *A61M 11/042* (2014.02); *A61M 15/009* (2013.01); *H05B 3/20* (2013.01); *A24F 40/10* (2020.01); *A61M 2205/0233* (2013.01); *H05B 2203/002* (2013.01); *H05B 2203/021* (2013.01)

(58) Field of Classification Search

CPC .......... A24F 40/46; A24F 40/44; A24F 40/42; A24F 40/10; H05B 3/20; H05B 2203/002; H05B 2203/021

USPC .......... 128/202.21

See application file for complete search history.

(56) References Cited

U.S. PATENT DOCUMENTS

| | | | | |
|---|---|---|---|---|
| 9,220,302 | B2 * | 12/2015 | DePiano | A24F 40/70 |
| 9,433,696 | B2 * | 9/2016 | Gruenbacher | B41J 2/1753 |
| 10,258,087 | B2 * | 4/2019 | Kane | H05B 3/56 |
| 10,368,399 | B2 * | 7/2019 | Tucker | A24F 40/40 |
| 10,455,863 | B2 * | 10/2019 | Rostami | A61M 11/042 |
| 10,750,784 | B2 * | 8/2020 | Mironov | F22B 1/284 |
| 10,905,168 | B2 * | 2/2021 | Force | A24F 40/48 |
| 11,051,552 | B2 * | 7/2021 | Mironov | F22B 1/284 |
| 2008/0092912 | A1 * | 4/2008 | Robinson | A24D 1/20 131/200 |
| 2008/0245305 | A1 | 10/2008 | Ikarashi et al. | |
| 2010/0181387 | A1 | 7/2010 | Zaffaroni et al. | |
| 2011/0023899 | A1 | 2/2011 | Strickland et al. | |
| 2011/0083676 | A1 | 4/2011 | Karles et al. | |
| 2013/0228191 | A1 * | 9/2013 | Newton | A24F 40/44 131/329 |
| 2015/0059780 | A1 | 3/2015 | Davis et al. | |
| 2015/0114409 | A1 | 4/2015 | Brammer et al. | |
| 2015/0208728 | A1 | 7/2015 | Lord | |
| 2015/0245669 | A1 | 9/2015 | Cadieux et al. | |
| 2015/0257447 | A1 | 9/2015 | Sullivan | |
| 2015/0367016 | A1 | 12/2015 | Gruenbacher et al. | |
| 2016/0143358 | A1 | 5/2016 | Zhu | |
| 2016/0330999 | A1 * | 11/2016 | Cameron | A61M 15/06 |
| 2016/0353802 | A1 | 12/2016 | Malgat et al. | |
| 2017/0020193 | A1 | 1/2017 | Davis et al. | |
| 2017/0035113 | A1 * | 2/2017 | Thorens | A24F 40/46 |
| 2017/0042243 | A1 | 2/2017 | Plojoux et al. | |
| 2017/0049153 | A1 | 2/2017 | Guo et al. | |
| 2017/0049154 | A1 | 2/2017 | Batista | |
| 2017/0181472 | A1 | 6/2017 | Batista et al. | |
| 2017/0188626 | A1 | 7/2017 | Davis et al. | |
| 2017/0196269 | A1 | 7/2017 | Bernauer et al. | |
| 2018/0007741 | A1 | 1/2018 | Metz et al. | |
| 2018/0035721 | A1 | 2/2018 | Cypher et al. | |
| 2018/0042301 | A1 | 2/2018 | Rostami | |
| 2019/0046741 | A1 | 2/2019 | Lord et al. | |
| 2021/0100286 | A1 | 4/2021 | Sudlow et al. | |
| 2022/0022543 | A1 * | 1/2022 | Campitelli | A24F 40/20 |

FOREIGN PATENT DOCUMENTS

| | | | |
|---|---|---|---|
| CN | 204796739 | U | 11/2015 |
| CN | 205180364 | U | 4/2016 |
| CN | 205250356 | U | 5/2016 |
| CN | 105873462 | A | 8/2016 |
| CN | 106490686 | A | 3/2017 |
| EP | 3135135 | A1 | 3/2017 |
| EP | 3332657 | A1 | 6/2018 |
| EP | 3711594 | A1 | 9/2020 |
| EP | 3711600 | A1 | 9/2020 |
| GB | 2504076 | A | 1/2014 |
| GB | 2561958 | A | 10/2018 |
| WO | 2011045672 | A1 | 4/2011 |
| WO | 2015077645 | A1 | 5/2015 |
| WO | 2015101479 | A1 | 7/2015 |
| WO | 2015114325 | A1 | 8/2015 |
| WO | 2015117704 | A1 | 8/2015 |
| WO | 2015117705 | A2 | 8/2015 |
| WO | 2015117705 | A3 | 10/2015 |
| WO | 2015177044 | A1 | 11/2015 |
| WO | 2016/061166 | | 4/2016 |
| WO | 2016/079152 | | 5/2016 |
| WO | 2016079155 | A1 | 5/2016 |
| WO | 2016096728 | A1 | 6/2016 |
| WO | 2016/135224 | | 9/2016 |
| WO | 2016145072 | A1 | 9/2016 |
| WO | 2016/156217 | | 10/2016 |
| WO | 2016154792 | A1 | 10/2016 |
| WO | 2016174179 | A1 | 11/2016 |
| WO | 2017001818 | A1 | 1/2017 |
| WO | 2017005471 | A1 | 1/2017 |
| WO | 2017093535 | A1 | 6/2017 |
| WO | 2017118927 | A1 | 7/2017 |
| WO | 2017/191176 | | 11/2017 |
| WO | 2017189883 | A1 | 11/2017 |
| WO | 2017220340 | A1 | 12/2017 |
| WO | 2018007625 | A1 | 1/2018 |
| WO | 2018197513 | A1 | 11/2018 |

OTHER PUBLICATIONS

Office Action for Chinese Application No. 201880039461.6 dated Feb. 9, 2022 (8 pages).

Office Action for United Kingdom Application No. GB1802836.5 dated Jul. 29, 2020 (3 pages).

Office Action for Chinese Application No. 201880039472.4 dated Mar. 31, 2022 (10 pages).

PCT International Search Report for PCT/EP2018/060503 dated Jun. 27, 2018; 12 Pages.

GB Search Report for GB1706593.9 dated Jul. 17, 2018; 9 Pages.

* cited by examiner

AEROSOL DELIVERY SYSTEM

CROSS-REFERENCE TO RELATED APPLICATIONS

This application is a US 371 application from PCT/EP2018/060503 Apr. 24, 2018, which claims priority from GB1706593.9 filed 25 Apr. 2017, the contents and elements of which are herein incorporated by reference for all purposes.

TECHNICAL FIELD

The present invention relates to an aerosol delivery system, a carrier for an aerosol precursor and a fluid-transfer article for an aerosol delivery system. In particular, the present invention relates to an aerosol delivery system comprising a heater configured to heat an aerosol precursor to generate an aerosolised composition for inhalation by a user.

BACKGROUND

Pharmaceutical medicament, physiologically active substances and flavourings for example may be delivered to the human body by inhalation through the mouth and/or nose. Such material or substances may be delivered directly to the mucosa or mucous membrane lining the nasal and oral passages and/or the pulmonary system. For example, nicotine is consumed for therapeutic or recreational purposes and may be delivered to the body in a number of ways. Nicotine replacement therapies are aimed at people who wish to stop smoking and overcome their dependence on nicotine. Nicotine is delivered to the body in the form of aerosol delivery devices and systems, also known as smoking-substitute devices or nicotine delivery devices. Such devices may be non-powered or powered.

Devices or systems that are non-powered may comprise nicotine replacement therapy devices such as "inhalators", e.g. Nicorette® Inhalator. These generally have the appearance of a plastic cigarette and are used by people who crave the behaviour associated with consumption of combustible tobacco—the so-called hand-to-mouth aspect—of smoking tobacco. Inhalators generally allow nicotine-containing aerosol to be inhaled through an elongate tube in which a container containing a nicotine carrier, for example, a substrate, is located. An air stream caused by suction through the tube by the user carries nicotine vapours into the lungs of the user to satisfy a nicotine craving. The container may comprise a replaceable cartridge, which includes a cartridge housing and a passageway in the housing in which a nicotine reservoir is located. The reservoir holds a measured amount of nicotine in the form of the nicotine carrier. The measured amount of nicotine is an amount suitable for delivering a specific number of "doses". The form of the nicotine carrier is such as to allow nicotine vapour to be released into a fluid stream passing around or through the reservoir. This process is known as aerosolization and or atomization. Aerosolization is the process or act of converting a physical substance into the form of particles small and light enough to be carried on the air i.e. into an aerosol. Atomization is the process or act of separating or reducing a physical substance into fine particles and may include the generation of aerosols. The passageway generally has an opening at each end for communication with the exterior of the housing and for allowing the fluid stream through the passageway. A nicotine-impermeable barrier seals the reservoir from atmosphere. The barrier includes passageway barrier portions for sealing the passageway on both sides of the reservoir. These barrier portions are frangible so as to be penetrable for opening the passageway to atmosphere.

A device or a system that is powered can fall into two sub-categories. In both sub-categories, such devices or systems may comprise electronic devices or systems that permit a user to simulate the act of smoking by producing an aerosol mist or vapour that is drawn into the lungs through the mouth and then exhaled. The electronic devices or systems typically cause the vaporization of a liquid containing nicotine and entrainment of the vapour into an airstream. Vaporization of an element or compound is a phase transition from the liquid phase to vapour i.e. evaporation or boiling. In use, the user experiences a similar satisfaction and physical sensation to those experienced from a traditional smoking or tobacco product, and exhales an aerosol mist or vapour of similar appearance to the smoke exhaled when using such traditional smoking or tobacco products.

A person of ordinary skill in the art will appreciate that devices or systems of the second, powered category as used herein include, but are not limited to, electronic nicotine delivery systems, electronic cigarettes, e-cigarettes, e-cigs, vaping cigarettes, pipes, cigars, cigarillos, vaporizers and devices of a similar nature that function to produce an aerosol mist or vapour that is inhaled by a user. Such nicotine delivery devices or systems of the second category incorporate a liquid reservoir element generally including a vaporizer or misting element such as a heating element or other suitable element, and are known inter alia, as atomizers, cartomizers, or clearomizers. Some electronic cigarettes are disposable; others are reusable, with replaceable and refillable parts.

Aerosol delivery devices or systems in a first sub-category of the second, powered Category generally use heat and/or ultrasonic agitation to vaporize a solution comprising nicotine and/or other flavouring, propylene glycol and/or glycerine-based base into an aerosol mist of vapour for inhalation.

Aerosol delivery devices or systems in a second sub-category of the second, powered category may typically comprise devices or systems in which tobacco is heated rather than combusted. During use, volatile compounds may be released from the tobacco by heat transfer from the heat source and entrained in air drawn through the aerosol delivery device or system. Direct contact between a heat source of the aerosol delivery device or system and the tobacco heats the tobacco to form an aerosol. As the aerosol containing the released compounds passes through the device, it cools and condenses to form an aerosol for inhalation by the user. In such devices or systems, heating, as opposed to burning, the tobacco may reduce the odour that can arise through combustion and pyrolytic degradation of tobacco.

Aerosol delivery devices or systems falling into the first sub-category of powered devices or system may typically comprise a powered unit, comprising a heater element, which is arranged to heat a portion of a carrier that holds an aerosol precursor. The carrier comprises a substrate formed of a "wicking" material, which can absorb aerosol precursor liquid from a reservoir and hold the aerosol precursor liquid. Upon activation of the heater element, aerosol precursor liquid in the portion of the carrier in the vicinity of the heater element is vaporised and released from the carrier into an airstream flowing around the heater and carrier. Released aerosol precursor is entrained into the airstream to be borne by the airstream to an outlet of the device or system, from where it can be inhaled by a user.

The heater element is typically a resistive coil heater, which is wrapped around a portion of the carrier and is usually located in the liquid reservoir of the device or system. Consequently, the surface of the heater may always be in contact with the aerosol precursor liquid and long-term exposure may result in the degradation of either or both of the liquid and heater. Furthermore, residues may build up upon the surface of the heater element, which may result in undesirable toxicants being inhaled by the user. Finally, as the level of liquid in the reservoir diminishes through use regions of the heater element may become exposed and overheat.

Aspects and embodiments of the invention were devised with the foregoing in mind.

BRIEF SUMMARY OF THE PRESENT INVENTION

According to an aspect of the present invention, there is provided an aerosol delivery system comprising: an aerosol-generation apparatus comprising: a receptacle for receiving a carrier; a heater; a carrier for an aerosol precursor comprising: a housing for location in said receptacle, said housing configured to provide a fluid pathway between a first end that is disposed in fluid engagement with an inlet of said aerosol-generating apparatus and a second end that is disposed in fluid engagement with an outlet of said aerosol-generating apparatus; and a fluid-transfer article located within said housing, said fluid-transfer article comprising a first region for holding an aerosol precursor and for transferring said aerosol precursor to an activation surface of a second region of said article, said activation surface disposed at an end of said carrier configured for thermal interaction with a heater of said aerosol-generation apparatus; wherein said second region comprises at least one discontinuity in said activation surface to form a corresponding at least one channel between said activation surface and an opposing surface through which heat is conveyable to said activation surface from said heater, said at least one channel configured for providing a fluid pathway across said activation surface, said fluid pathway across said activation surface forming a portion of said fluid pathway between said first end and said second end.

Optionally, said article may comprise a tubular member. Further optionally, said article may comprise a bore extending therethrough, said first region extending axially along an external surface of said article and said second surface, located between said first region and said bore, extending axially along an internal surface of said article, said at least one discontinuity extending axially along said internal surface of said article formed by said bore. Yet further optionally, said article may comprise a bore extending therethrough, said first region extending axially along an internal surface of said article and said second surface extending axially along an external surface of said article, said at least one discontinuity extending axially at least partially along said external surface of said article.

Optionally, an end surface of said tubular member may comprise said activation surface and further wherein said at least one discontinuity may extend radially across said activation surface.

Optionally, an end surface of said tubular member may comprise said activation surface and further wherein said at least one discontinuity may extend linearly across said activation surface.

Optionally, an end surface of said tubular member may comprise said activation surface and further wherein said at least one discontinuity may be convolute, meandering and/or serpentine across said activation surface.

Optionally, said activation surface may be formed at an interface between regions adjacent said at least one discontinuity and said opposing surface through which heat is conveyed to said activation surface from said heater.

Optionally, said heater may comprise a planar heating surface.

Optionally, said heater may be a rod extending axially through said centre of said fluid transfer article.

Optionally, said heater may comprise a collar arranged around said article.

Optionally, said collar may extend over a length of said article. Optionally, said collar may extend over said second region of said article.

Optionally, said heater may comprise said opposing surface through which heat is conveyed to said activation surface, said heater in contact with said activation surface of said article.

Optionally, a thermally conductive barrier layer may be provided as said opposing surface through which heat is conveyable to said activation surface, said thermally conductive barrier layer in thermal contact with said heater and located between said heater and said activation surface of said article.

Optionally, said activation surface and said opposing surface through which heat is conveyable to said activation surface may be complementary. This may maintain a temperature gradient through the at least one channel for consistency of activation.

Optionally, said activation surface and said heater surface may be complementary.

Optionally, said article may be formed of a thermally conductive material.

Optionally, said article may be formed of a plastic material, such as, for example, Polyetherimide or Polytetratluoroethylene (PTFE). Other suitable materials may comprise, for example, BioVyon™ (by Porvair Filtration Group Ltd) and materials available from Porex®. Further optionally, a substrate forming the fluid-transfer article may comprise polypropylene or polyethylene terephthalate.

Optionally, said article may be formed from a hydrophilic material that is configured to transfer fluid from said first region to said second region.

Optionally, said article may be formed from a sintered material.

Optionally, said article may comprise a plurality of regions having different structures Optionally, said article may be formed of a porous material in which pore diameter in said first region is greater than pore diameter in said second region.

Optionally, said article may be formed of a material that is of greater hydrophilicity in said second region than said first region.

Optionally, said article may be formed of a wicking material comprising a graduated wicking action.

Optionally, said heater may comprise a material of at least one of: a ceramic; and a metal.

Optionally, a first end and a second end of said housing may be sealed with a removable end cap. The end caps are removable prior to the carrier being located in said apparatus.

Optionally, a first end and a second end of said housing may be sealed with a frangible barrier portion. The frangible barrier portion may be frangible so as to be penetrable for opening said carrier to atmosphere.

According to another aspect of the present invention, there is provided an aerosol-generation apparatus for use in the system as described above and hereinafter.

According to another aspect of the present invention, there is provided a carrier for an aerosol precursor comprising: a housing for location in a receptacle of an aerosol-generating apparatus, said housing configured to provide a fluid pathway between a first end that is disposed in fluid engagement with an inlet of said aerosol-generating apparatus and a second end that is disposed in fluid engagement with an outlet of said aerosol-generating apparatus; and a fluid-transfer article located within said housing, said fluid-transfer article comprising a first region for holding an aerosol precursor and for transferring said aerosol precursor to an activation surface of a second region of said article, said activation surface disposed at an end of said carrier configured for thermal interaction with a heater of an aerosol-generation apparatus; wherein said second region comprises at least one discontinuity in said activation surface to form a corresponding at least one channel between said activation surface and an opposing surface through which heat is conveyable to said activation surface from a heater, said at least one channel configured for providing a fluid pathway across said activation surface, said fluid pathway across said activation surface forming a portion of said fluid pathway between said first end and said second end. Optionally, the article may comprise a tubular member.

Optionally, said article may comprise a bore extending therethrough, said first region extending axially along an external surface of said article and said second surface, located between said first region and said bore, extending axially along an internal surface of said article, said at least one discontinuity extending axially along said internal surface of said article formed by said bore.

Optionally, said article may comprise a bore extending therethrough, said first region extending axially along an internal surface of said article and said second surface extending axially along an external surface of said article, said at least one discontinuity extending axially at least partially along said external surface of said article.

Optionally, an end surface of said tubular member may comprise said activation surface and further wherein said at least one discontinuity may extend radially across said activation surface.

Optionally, an end surface of said tubular member may comprise said activation surface and further wherein said at least one discontinuity may extend linearly across said activation surface.

Optionally, an end surface of said tubular member may comprise said activation surface and further wherein said at least one discontinuity may be convolute, meandering and/or serpentine across said activation surface.

Optionally, said activation surface may be formed at an interface between regions adjacent said at least one discontinuity and said opposing surface through which heat is conveyed to said activation surface from a heater.

Optionally, a thermally conductive barrier layer may be provided as said opposing surface through which heat is conveyable to said activation surface, said thermally conductive barrier layer configured for thermal contact with a heater and locatable between a heater and said activation surface of said article.

Optionally, said activation surface and said opposing surface through which heat is conveyable to said activation surface may be complementary. This may maintain a temperature gradient through the at least one channel for consistency of activation.

Optionally, said article may be formed of a thermally conductive material.

Optionally, said article may be formed of a plastic material, such as, for example, Polyetherimide or Polytetrafluoroethylene (PTFE). Other suitable materials may comprise, for example, BioVyon™ (by Porvair Filtration Group Ltd) and materials available from Porex®. Further optionally, a substrate forming the fluid-transfer article may comprise polypropylene or polyethylene terephthalate.

Optionally, said article may be formed from a hydrophilic material that is configured to transfer fluid from said first region to said second region.

Optionally, said article may be formed from a sintered material.

Optionally, said article may comprise a plurality of regions having different structures.

Optionally, said article may be formed of a porous material in which pore diameter in said first region is greater than pore diameter in said second region.

Optionally, said article may be formed of a material that is of greater hydrophilicity in said second region than said first region.

Optionally, said article may be formed of a wicking material comprising a graduated wicking action.

Optionally, a first end and a second end of said housing may be sealed with a removable end cap. The end caps are removable prior to the carrier being located in said apparatus.

Optionally, a first end and a second end of said housing may be sealed with a frangible barrier portion. The frangible barrier portion may be frangible so as to be penetrable for opening said carrier to atmosphere.

According to another aspect of the present invention, there is provided a fluid-transfer article comprising: a first region for holding an aerosol precursor and for transferring said aerosol precursor to an activation surface of a second region of said article, said activation surface disposed at an end of said article configured for thermal interaction with a heater of an aerosol generation apparatus, wherein said second region comprises at least one discontinuity in said activation surface to form a corresponding at least one channel between said activation surface and an opposing surface through which heat is conveyable to said activation surface from a heater, said at least one channel configured for providing a fluid pathway across said activation surface, said fluid pathway across said activation surface forming a portion of said fluid pathway between said first end and said second end.

Optionally, the article may comprise a tubular member.

Optionally, the article may comprise a bore extending therethrough, said first region extending axially along an external surface of said article and said second surface, located between said first region and said bore, extending axially along an internal surface of said article, said at least one discontinuity extending axially along said internal surface of said article formed by said bore.

Optionally, said article may comprise a bore extending therethrough, said first region extending axially along an internal surface of said article and said second surface extending axially along an external surface of said article, said at least one discontinuity extending axially at least partially along said external surface of said article.

Optionally, an end surface of said tubular member may comprise said activation surface and further wherein said at least one discontinuity may extend radially across said activation surface.

Optionally, an end surface of said tubular member may comprise said activation surface and further wherein said at least one discontinuity may extend linearly across said activation surface.

Optionally, an end surface of said tubular member may comprise said activation surface and further wherein said at least one discontinuity may be convolute, meandering and/or serpentine across said activation surface.

Optionally, said activation surface may be formed at an interface between regions adjacent said at least one discontinuity and said opposing surface through which heat is conveyed to said activation surface from a heater.

Optionally, a thermally conductive barrier layer may be provided as said opposing surface through which heat is conveyable to said activation surface, said thermally conductive barrier layer configured for thermal contact with a heater and locatable between a heater and said activation surface of said article.

Optionally, said activation surface and said opposing surface through which heat is conveyable to said activation surface may be complementary. This may maintain a temperature gradient through the at least one channel for consistency of activation.

Optionally, said article may be formed of a thermally conductive material.

Optionally, said article may be formed of a plastic material, such as, for example, Polyetherimide or Polytetrafluoroethylene (PTFE). Other suitable materials may comprise, for example, BioVyon™ (by Porvair Filtration Group Ltd) and materials available from Porex®. Further optionally, a substrate forming the fluid-transfer article may comprise polypropylene or polyethylene terephthalate.

Optionally, said article may be formed from a hydrophilic material that is configured to transfer fluid from said first region to said second region.

Optionally, said article may be formed from a sintered material.

Optionally, said article may comprise a plurality of regions having different structures.

Optionally, said article may be formed of a porous material in which pore diameter in said first region is greater than pore diameter in said second region.

Optionally, said article may be formed of a material that is of greater hydrophilicity in said second region than said first region.

Optionally, said article may be formed of a wicking material comprising a graduated wicking action.

According to another aspect of the present invention, there is provided a kit-of-parts for assembling a system for aerosol delivery, comprising: an aerosol-generation apparatus comprising a receptacle for receiving a carrier; a heater; a carrier for an aerosol precursor, said carrier locatable in said receptacle, and said carrier comprising a housing for location in said receptacle, said housing configured to provide a fluid pathway between a first end that is disposed in fluid engagement with an inlet of said aerosol-generating apparatus and a second end that is disposed in fluid engagement with an outlet of said aerosol-generating apparatus; and a fluid-transfer article located within said housing, said fluid-transfer article comprising a first region for holding an aerosol precursor and for transferring said aerosol precursor to an activation surface of a second region of said article, said activation surface disposed at an end of said carrier configured for thermal interaction with a heater of said aerosol-generation apparatus; wherein said second region comprises at least one discontinuity in said activation surface to form a corresponding at least one channel between said activation surface and an opposing surface through which heat is conveyable to said activation surface from said heater, said at least one channel configured for providing a fluid pathway across said activation surface, said fluid pathway across said activation surface forming a portion of said fluid pathway between said first end and said second end.

BRIEF DESCRIPTION OF THE DRAWINGS

One or more embodiments in accordance with aspects of the present invention will be described, by way of example only, and with reference to the following drawings in which:

FIG. 9b is a perspective cross-section side view of the aerosol carrier of FIG. 9a.

DETAILED DESCRIPTION OF THE INVENTION

In general outline, one or more embodiments in accordance with the present invention provide a system for aerosol delivery in which an aerosol carrier may be inserted into a receptacle (e.g. a "beating chamber") of an apparatus for initiating and maintaining release of an aerosol from the aerosol carrier. Another end, or another end portion, of the aerosol carrier may protrude from the apparatus and can be inserted into the mouth of a user for the inhalation of aerosol released from the aerosol carrier cartridge during operation of the apparatus.

Hereinafter, and for convenience only, "system for aerosol delivery" shall be referred to as "aerosol delivery system".

Figure 1:
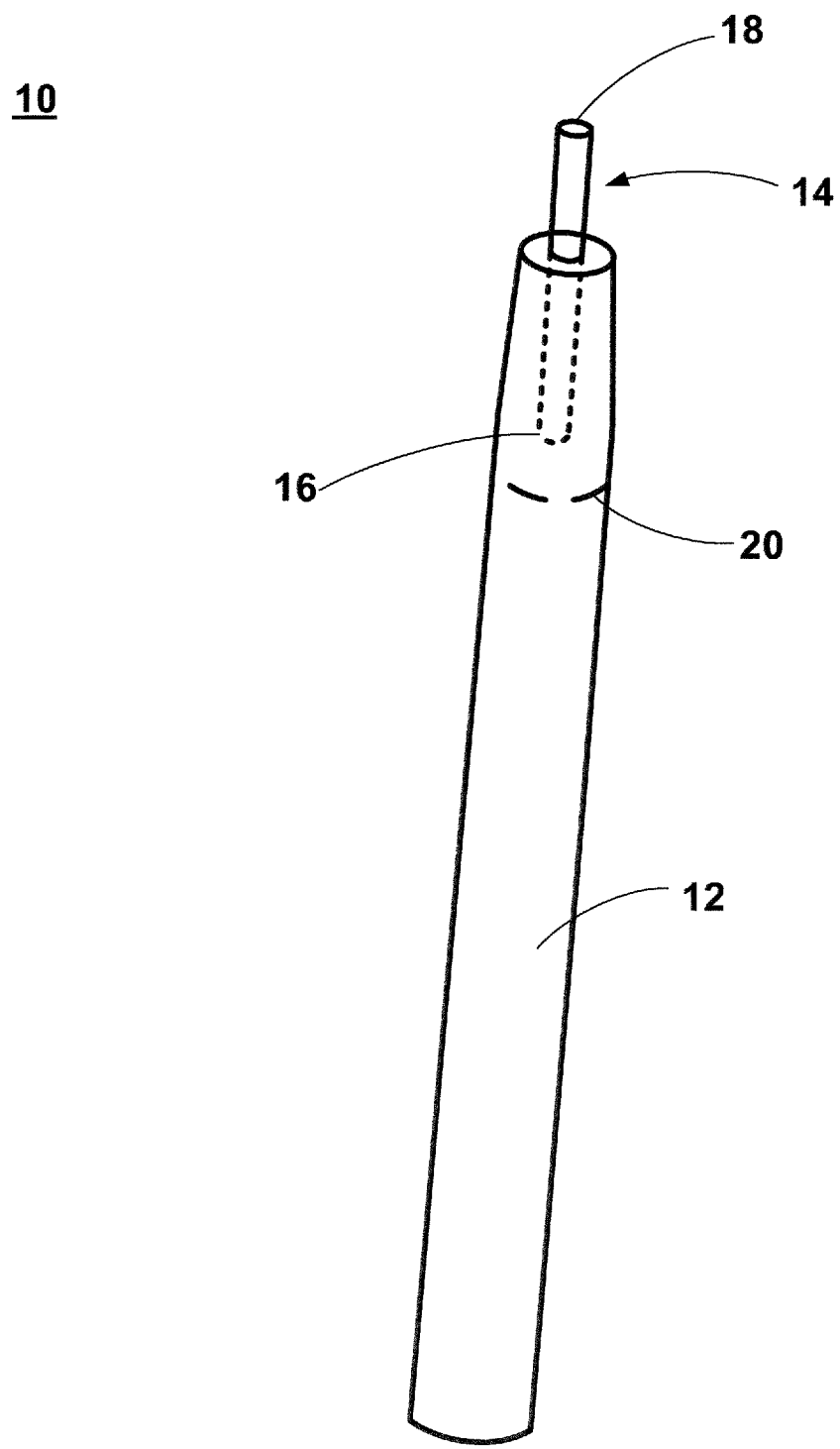
FIG. 1 is a perspective view illustration of a system for aerosol delivery according to one or more embodiments of the present invention.

Referring now to FIG. 1, there is a perspective view of an aerosol delivery system 10 comprising an aerosol generation apparatus 12 operative to initiate and maintain release of aerosol from a fluid-transfer article in an aerosol carrier 14. In FIG. 1, the aerosol carrier 14 is shown with a first end 16 thereof and a portion of the length of the aerosol carrier 14 located within a receptacle of the apparatus 12. A remaining portion of the aerosol carrier 14 extends out of the receptacle. This remaining portion of the aerosol carrier 14, terminating at a second end 18 of the aerosol carrier, is configured for insertion into a user's mouth. A vapour and/or aerosol is produced when a heater (not shown) of the apparatus 12 heats a fluid-transfer article in the aerosol carrier 14 to release a vapour and/or an aerosol, and this can be delivered to the user, when the user sucks or inhales, via a fluid passage in communication with an outlet of the aerosol carrier 14 from the fluid-transfer article to the second end 18.

The device 12 also comprises air-intake apertures 20 in the housing of the apparatus 12 to provide a passage for air to be drawn into the interior of the apparatus 12 (when the user sucks or inhales) for delivery to the first end 16 of the aerosol carrier 14, so that the air can be drawn across an activation surface of a fluid-transfer article located within a housing of the aerosol carrier cartridge 14 during use. Optionally, these apertures may be perforations in the housing of the apparatus 12.

A fluid-transfer article (not shown in FIG. 1, but see FIGS. 5, 6, 7a, 7b, 8a, 8b, 9a and 9b) is located within a housing of the aerosol carrier 14. The fluid-transfer article contains an aerosol precursor material, which may include at least one of: nicotine; a nicotine precursor material; a nicotine compound; and one or more flavourings. The fluid-transfer article is located within the housing of the aerosol carrier 14 to allow air drawn into the aerosol carrier 14 at, or proximal, the first end 16 to flow across an activation surface of the fluid-transfer article. As air passes across the activation surface of the fluid-transfer article, an aerosol may be entrained in the air stream from a substrate forming the fluid-transfer article, e.g. via diffusion from the substrate to the air stream and/or via vaporisation of the aerosol precursor material and release from the fluid-transfer article under heating.

The substrate forming the fluid-transfer article comprises a porous material where pores of the porous material hold, contain, carry, or bear the aerosol precursor material. Optionally, the porous material may comprise a sintered material such as, for example, Polyetherimide or Polytetrafluoroethylene (PTFE). Other suitable materials may comprise, for example, BioVyon™ (by Porvair Filtration Group Ltd) and materials available from Porex®. Further optionally, a substrate forming the fluid-transfer article may comprise polypropylene or polyethylene terephthalate.

The aerosol carrier 14 is removable from the apparatus 12 so that it may be disposed of when expired. After removal of a used aerosol carrier 14 a replacement aerosol carrier 14 can be inserted into the apparatus 12 to replace the used aerosol carrier 14.

Figure 2:
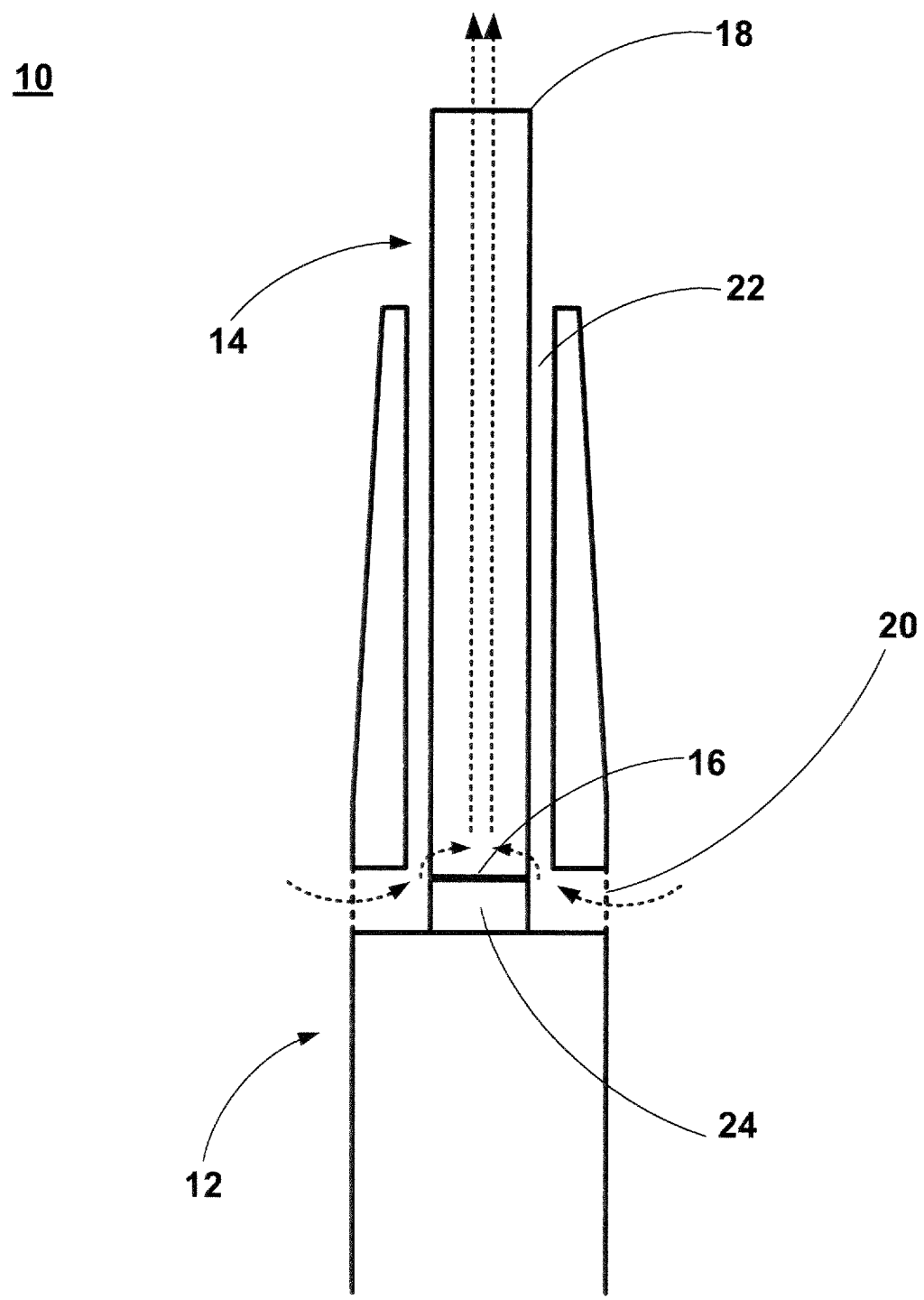
FIG. 2 is a cross-sectional side view illustration of part of an apparatus of the system for aerosol delivery of FIG. 1.

FIG. 2 is a cross-sectional side view illustration of a part of apparatus 12 of the aerosol delivery system 10.

The apparatus 12 comprises a receptacle 22 in which is located a portion of the aerosol carrier 14. In one or more optional arrangements, the receptacle 22 may enclose the aerosol carrier 14.

The apparatus 12 also comprise a heater 24, which opposes an activation surface of the fluid-transfer article (not shown) of the aerosol carrier 14 when an aerosol carrier 14 is located within the receptacle 22.

Air flows into the apparatus 12 (in particular, into a closed end of the receptacle 22) via air-intake apertures 20. From the closed end of the receptacle 22, the air is drawn into the aerosol carrier 14 (under the action of the user inhaling or sucking on the second end 18) and expelled at second end 18. As the air flows into the aerosol carrier 14, it passes across the activation surface of the fluid-transfer article. Heat from the heater 24, which opposes the activation surface of the fluid-transfer article, causes vaporisation of aerosol precursor material at the activation surface of the fluid-transfer article and an aerosol is created in the air flowing over the activation surface. Thus, through the application of heat in the region of the activation surface of the fluid-transfer article, an aerosol is released, or liberated, from the fluid-transfer article, and is drawn from the material of the aerosol carrier unit by the air flowing across the activation surface and is transported in the air flow to via outlet conduits (not shown) in the housing of the aerosol carrier 14 to the second end 18. The direction of air flow is illustrated by arrows in FIG. 2.

Figure 3:
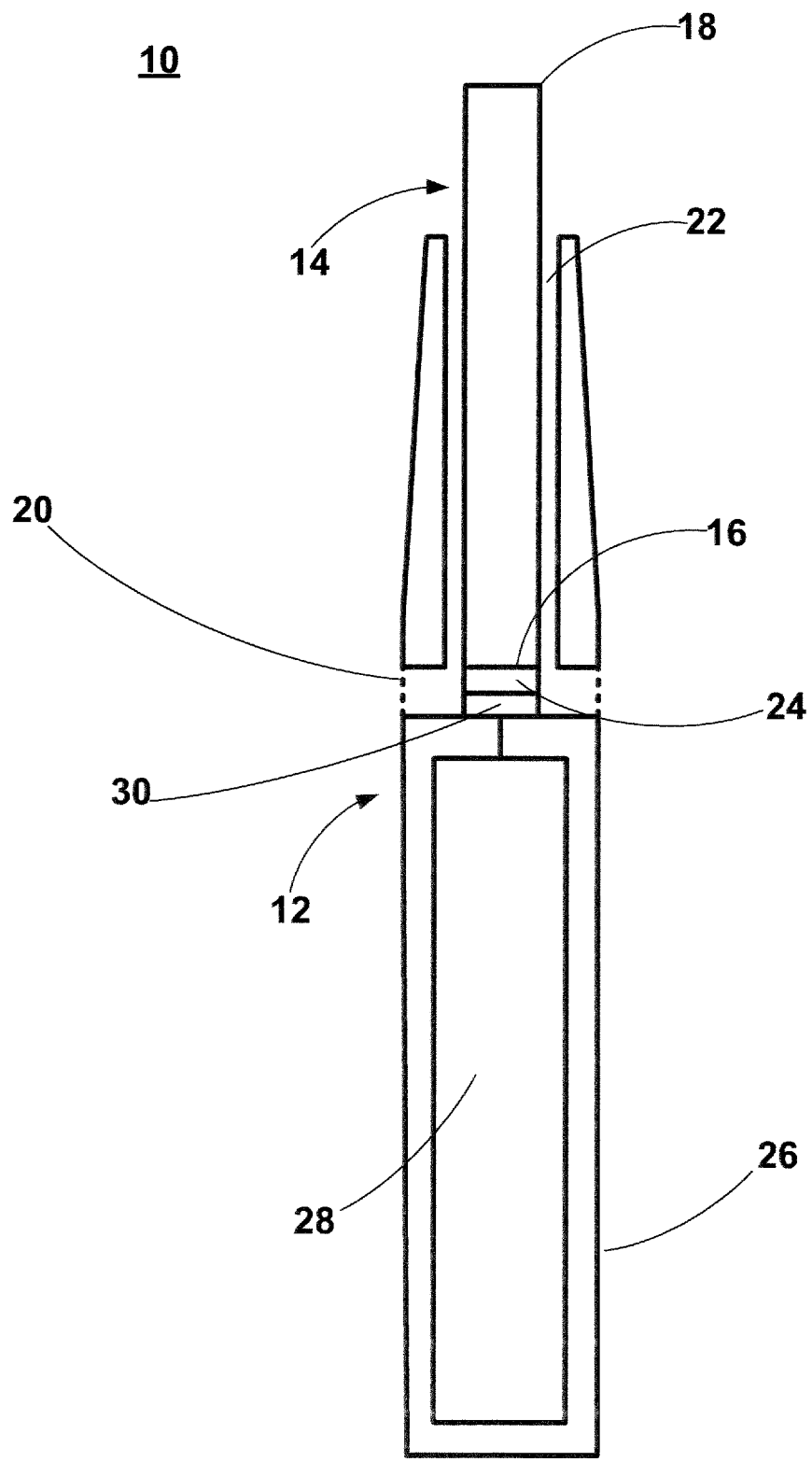
FIG. 3 is a cross-sectional side view illustration of the system and apparatus for aerosol delivery of FIG. 1.

To achieve release of the captive aerosol from the fluid-transfer article, the fluid-transfer article of the aerosol carrier 14 is heated by the heater 24. As a user sucks or inhales on second end 18 of the aerosol carrier 14, the aerosol released from the fluid-transfer article and entrained in the air flowing across the activation surface of the fluid-transfer article is drawn through the outlet conduits (not shown) in the housing of the aerosol carrier 14 towards the second end 18 and onwards into the user's mouth. Turning now to FIG. 3, a cross-sectional side view of the aerosol delivery system 10 is schematically illustrated showing the features described above in relation to FIGS. 1 and 2 in more detail.

As can be seen, apparatus 12 comprises a housing 26, in which are located the receptacle 22 and heater 24. The housing 26 also contains control circuitry (not shown) operative by a user, or upon detection of air and/or vapour being drawn into the device 12 through air-intake apertures 20, i.e. when the user sucks or inhales. Additionally, the housing 26 comprises an electrical energy supply 28, for example a battery. Optionally, the battery comprises a rechargeable lithium ion battery. The housing 26 also comprises a coupling 30 for electrically (and optionally mechanically) coupling the electrical energy supply 28 to control circuitry (not shown) for powering and controlling operation of the heater 24.

Responsive to activation of the control circuitry of apparatus 12, the heater 24 heats the fluid-transfer article (not shown) of aerosol carrier 14. This heating process initiates (and, through continued operation, maintains) release of vapour and/or an aerosol from the activation surface of the fluid-transfer article. The vapour and/or aerosol formed as a result of the heating process is entrained into a stream of air being drawn across the activation surface of the fluid-transfer article (as the user sucks or inhales). The stream of air with the entrained vapour and/or aerosol passes through the aerosol carrier 14 via outlet conduits (not shown) and exits the aerosol carrier 14 at second end 18 for delivery to the user.

This process is briefly described above in relation to FIG. 2, where arrows schematically denote the flow of the air stream into the device 12 and through the aerosol carrier 14 and the flow of the air stream with the entrained vapour and/or aerosol through the aerosol carrier cartridge 14.

Figure 4:
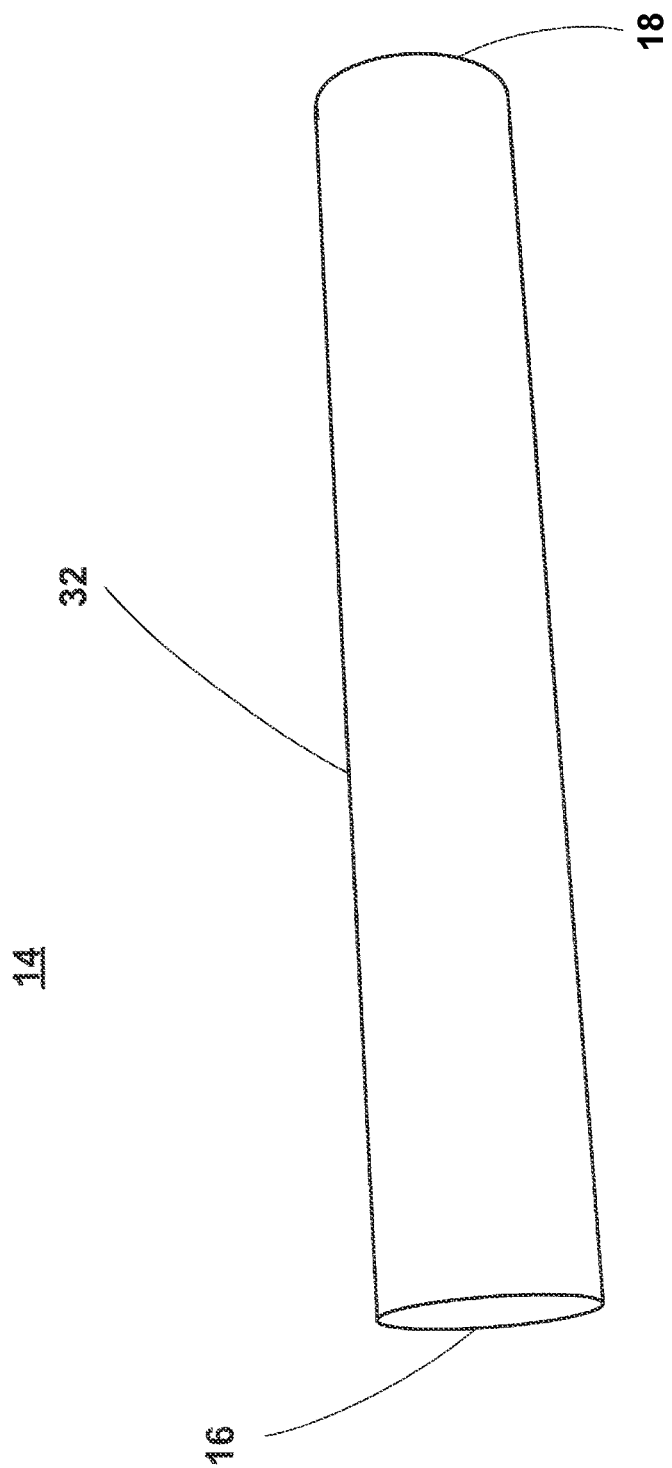
FIG. 4 is a perspective view illustration of an aerosol carrier for use in the system for aerosol delivery according to one or more embodiments of the present invention.
Figure 5:
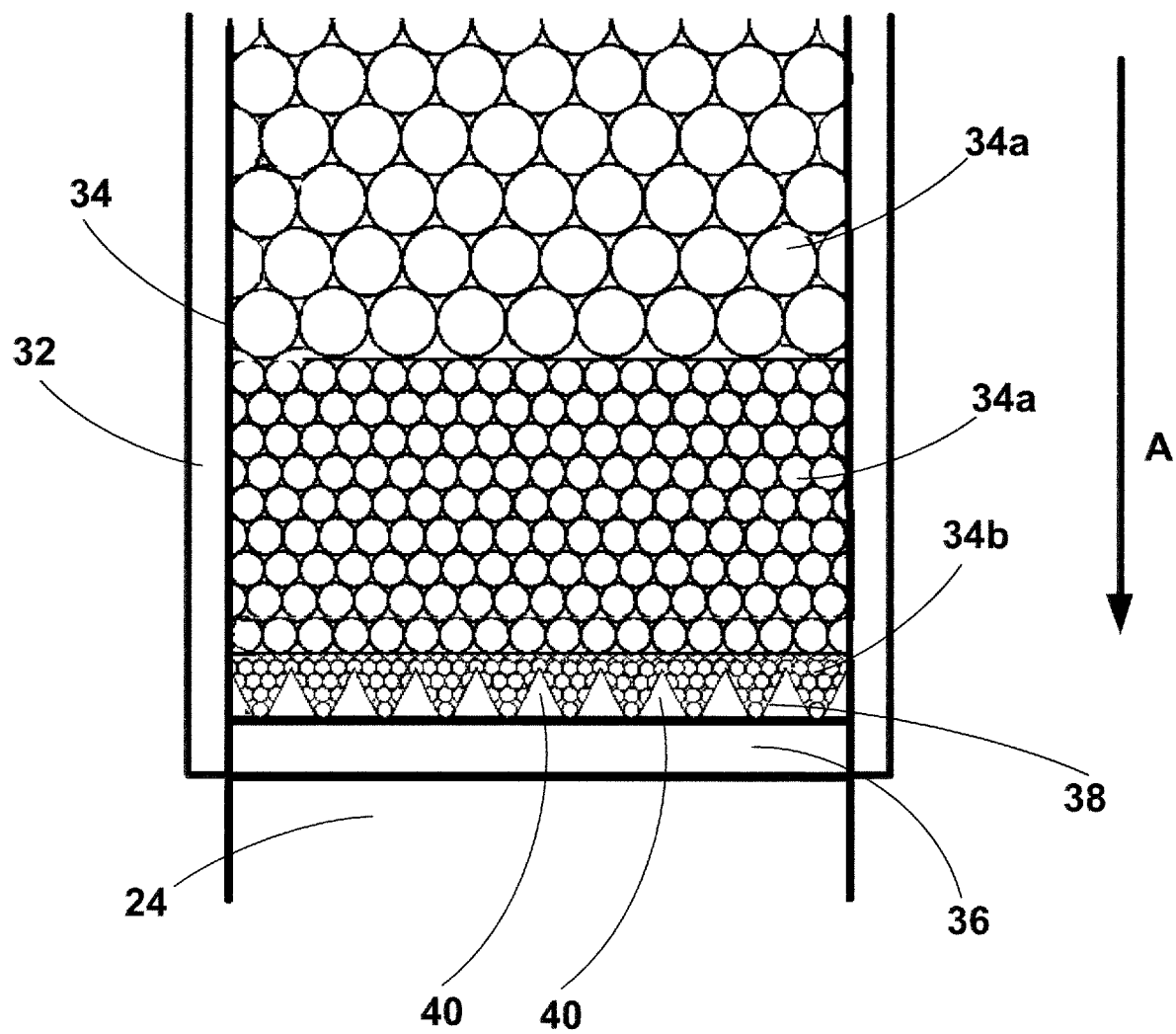
FIG. 5 is a cross-section side view of elements of an aerosol carrier and of part of an apparatus of the system for aerosol delivery according to one or more embodiments of the present invention.
Figure 6:
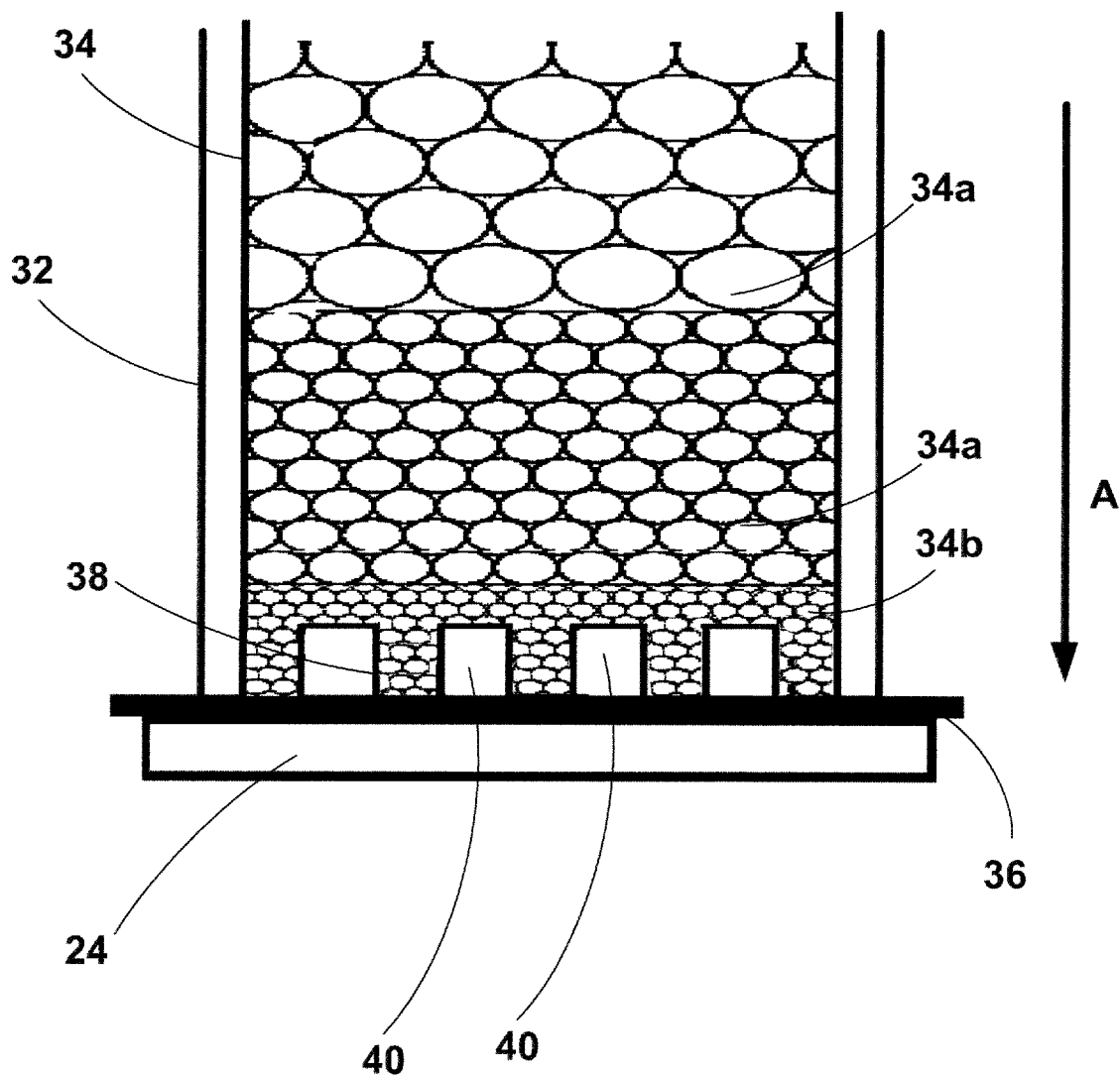
FIG. 6 is a cross-section side view of elements of an aerosol carrier and of part of an apparatus of the system for aerosol delivery according to one or more embodiments of the present invention.

FIGS. 4 to 6 schematically illustrate the aerosol carrier 14 in more detail (and, in FIGS. 5 and 6, features within the receptacle in more detail). FIG. 4 illustrates an exterior of the aerosol carrier 14, FIG. 5 illustrates internal components of the aerosol carrier 14 in an optional arrangement of one or more embodiments of the present invention, and FIG. 6 illustrates internal components of the aerosol carrier 14 in another optional arrangement of one or more embodiments of the present invention.

FIG. 4 illustrates the exterior of the aerosol carrier 14, which comprises housing 32 for housing said fluid-transfer article (not shown) and at least one other internal component. The housing 32 comprises a tubular member, which may be generally cylindrical in form, and which is configured to be received within the receptacle of the apparatus. First end 16 of the aerosol carrier 14 is for location to oppose the heater of the apparatus and second end 18 (and the region adjacent the second end 18) is configured for insertion into a user's mouth.

FIG. 5 illustrates some internal components of the aerosol carrier 14 and of the heater 24 of apparatus 12. As described above, the aerosol carrier 14 comprises a fluid-transfer article 34. The aerosol carrier 14 optionally may comprise a conduction element 36 (i.e. as shown in FIG. 5). In one or more embodiments, the aerosol carrier 14 is located within the receptacle of the apparatus such that the activation surface of the fluid-transfer article opposes the heater of the apparatus and receives heat directly from the heater of the apparatus. In an optional arrangement, such as illustrated in FIG. 5 for example, the aerosol carrier 14 comprises a conduction element 36. When aerosol carrier 14 is located within the receptacle of the apparatus such that the activation surface of the fluid-transfer article is located to oppose the heater of the apparatus, the conduction element is disposed between the heater 24 and activation surface of the fluid-transfer article. Heat may be transferred to the activation surface via conduction through conduction element 36 (i.e. application of heat to the activation surface is indirect)

Further components not shown in FIGS. 5 and 6 (see FIGS. 9a and 9b) comprise an inlet conduit, via which air can be drawn into the aerosol carrier 14, an outlet conduit, via which an air stream entrained with aerosol can be drawn from the aerosol carrier 14, a filter element, and a reservoir for storing aerosol precursor material and for providing the aerosol precursor material to the fluid-transfer article 34.

In FIGS. 5 and 6, aerosol carrier is shown as comprising the fluid-transfer article 34 located within housing 32. The material forming the fluid transfer article comprises a porous structure, where pore diameter size varies between one end of the fluid-transfer article 34 and another end of the fluid-transfer article. In the illustrative examples of FIGS. 5 and 6, the pore diameter size gradually decreases from a first end remote from heater 24 (the upper end as shown in the figure) to a second end proximal heater 24 (the lower end as shown in the figure). Although the figure illustrates the pore diameter size changing in a step-wise manner from the first to the second end (i.e. a first region with pores having a diameter of a first size, a second region with pores having a diameter of a second, smaller size, and a third region with pores having a diameter of a third, yet smaller size), the change in pore size from the first end to the second end may be gradual rather than step-wise. This configuration of pores having a decreasing diameter size from the first end and second end can provide a wicking effect, which can serve to draw fluid from the first end to the second end of the fluid-transfer article 34.

The fluid-transfer article 34 comprises a first region 34a for holding an aerosol precursor. In one or more embodiments, the first region 34a of the fluid-transfer article 34 comprises a reservoir for holding the aerosol precursor. The first region 34a can be the sole reservoir of the aerosol carrier 14, or it can be arranged in fluid communication with a separate reservoir, where aerosol precursor is stored for supply to the first region 34a.

The fluid-transfer article 34 also comprises a second region 34b. Aerosol precursor is drawn from the first region 34a to the second region 34b by the wicking effect of the substrate material forming the fluid transfer article. Thus, the first region is configured to transfer the aerosol precursor to the second region of the article.

At the second end of fluid-transfer article 34, surface of the second region 34b comprises an activation surface 38, which is disposed opposite a surface for conveying heat to the activation surface 38. In the illustrative examples of FIGS. 5 and 6, the opposing surface for conveying heat to the activation surface 38 comprises a conduction element 36.

Conduction element 36 is located for thermal interaction with heater 24 and is arranged to transfer heat from heater 24 to the activation surface 38. As noted above, however, the conduction element 36 may be absent in one or more embodiments and so activation surface 38 is disposed to receive heat directly from heater 24 in one or more embodiments.

The conduction element 36 may comprise a thin film thermally conductive material, such as, for example, a metal foil. For example, aluminium, brass, copper, gold, steel, silver, or an alloy comprising any one of the foregoing together with thermally conductive plastics and/or ceramics.

The activation surface 38 is discontinuous such that at least one channel 40 is formed between the activation surface 38 and the conduction element 36 (or the heater 24 in one or more embodiments where the conduction element 36 is absent). In one or more embodiments, the discontinuities may be such that the activation surface is undulating.

In the illustrative examples of FIGS. 5 and 6, the activation surface 38 comprises a plurality of grooves or valleys therein to form an undulating surface, the grooves or valleys disposed in a parallel arrangement across the activation surface 38. Thus, there are a plurality of channels 40 between the activation surface 38 and the conduction element 36.

In the illustrative example of FIG. 5, the grooves or valleys in the activation surface 38 provide alternating peaks and troughs that give rise to a "sawtooth" type profile. In one or more optional arrangements, the activation surface may comprise a "castellated" type profile (i.e. a "square wave" type profile), for example, such as illustrated in the example of FIG. 6. In one or more optional arrangements, the activation surface may comprise a "sinusoidal" type profile. The profile may comprise a mixture of two or more of the above profiles given as illustrative examples.

In the illustrative examples of FIGS. 5 and 6, the first region 34a of the fluid-transfer article 34 is located at an "upstream" end of the fluid-transfer article 34 and the second region 34b is located at a "downstream" end of the fluid-transfer article 34. That is, aerosol precursor is wicked, or is drawn, from the "upstream" end of the fluid-transfer article 34 to the "downstream" end of the fluid-transfer article 34 (as denoted by arrow A in FIG. 5).

The aerosol precursor is configured to release an aerosol and/or vapour upon heating. Thus, when the activation surface 38 receives heat conveyed from heater 24, the aerosol precursor held at the activation surface 38 is heated. The aerosol precursor, which is captively held in material of the fluid-transfer article at the activation surface 38 is released into an air stream flowing through the channels 40 between the conduction element 36 and activation surface 38 (or between the heater 24 and the activation surface 38) as an aerosol and/or vapour.

The shape and/or configuration of the activation surface 38 and the associated shape(s) and/or configuration(s) of the one or more channels formed between the activation surface 38 and conduction element 36 (or between the activation surface 38 and heater 24) permit air to flow across the activation surface 38 (through the one or more channels 40) and also increase the surface area of the activation surface 38 of the fluid-transfer article 34 that is available for contact with a flow of air across the activation surface 38.

Figure 7A:
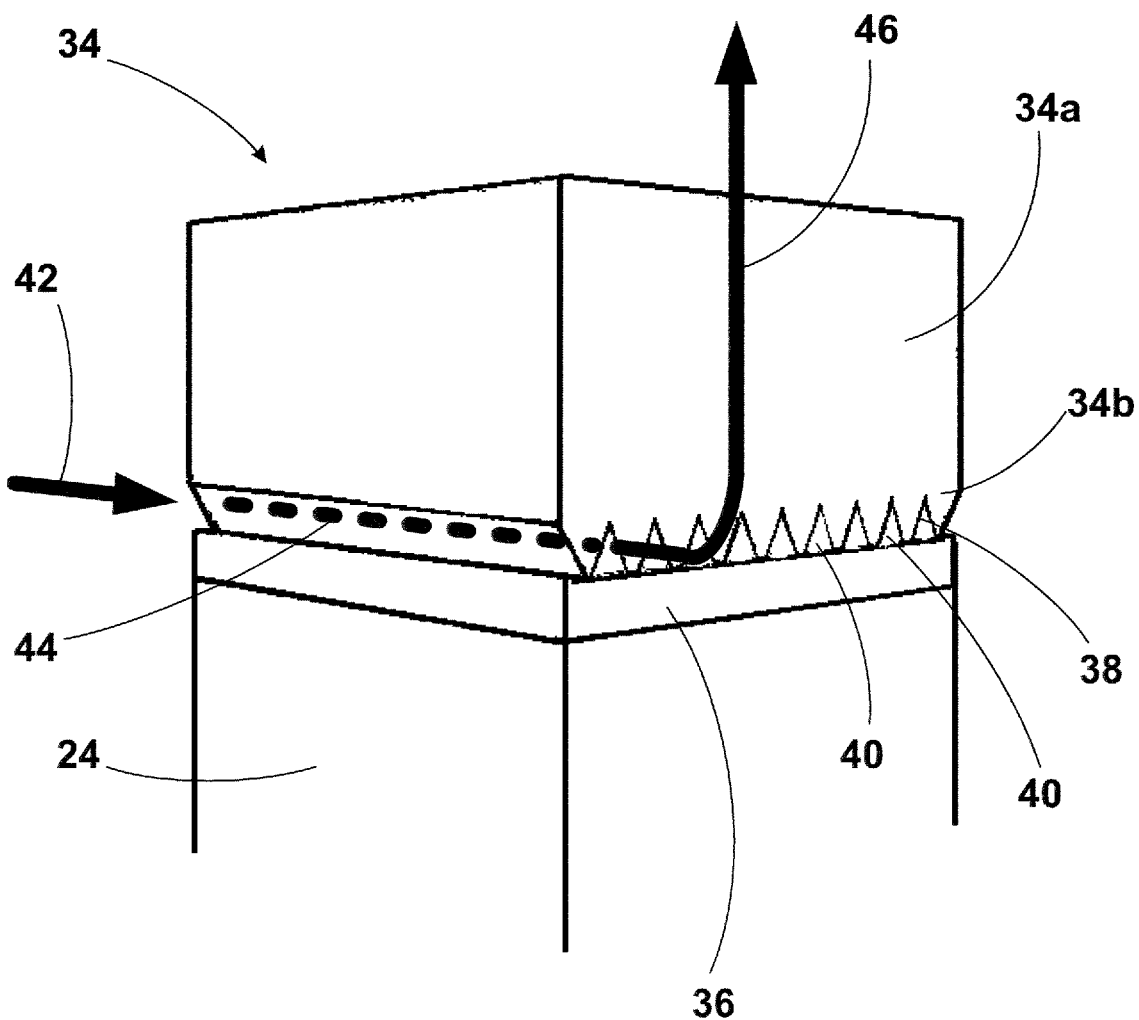
FIG. 7a is a perspective view illustration of the aerosol carrier and of part of an apparatus of the system for aerosol delivery according to one or more embodiments of the present invention.
Figure 7B:
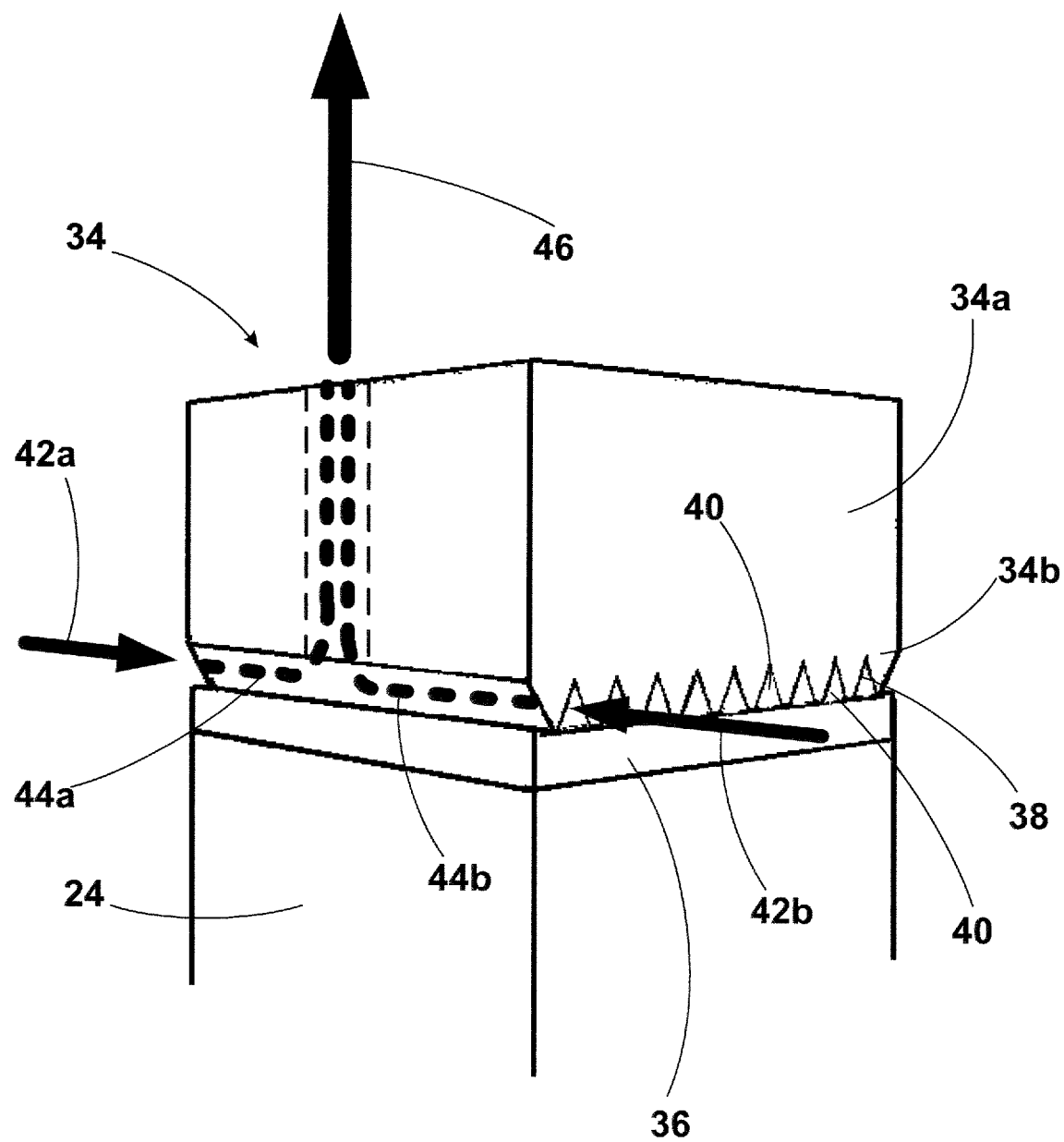
FIG. 7b is a perspective view illustration of the aerosol carrier and of part of an apparatus of the system for aerosol delivery according to one or more embodiments of the present invention.

FIGS. 7a and 7b show perspective view illustrations of the fluid-transfer article 34 of aerosol carrier and a heater 24 of the apparatus of the system for aerosol delivery according to one or more embodiments of the present invention. In particular, these figures illustrate air flows across the activation surface 38 when the apparatus is in use in a first arrangement of the fluid-transfer article 34 (see FIG. 7a) and in a second arrangement of the fluid-transfer article 34 (see FIG. 7b).

In the illustrated example of use of the apparatus schematically illustrated in FIG. 7a, when a user sucks on a mouthpiece of the apparatus, air is drawn into the carrier through inlet apertures (not shown) provided in a housing of the carrier. An incoming air stream 42 is directed to the activation surface 38 of the fluid-transfer article 34 (e.g. via a fluid communication pathway within the housing of the carrier). When the incoming air stream 42 reaches a first side of the activation surface 38, the incoming air stream 42 flows across the activation surface 38 via the one or more channels 40 formed between the activation surface 38 and the conduction element 36 (or between the activation surface 38 and heater 24). The air stream flowing through the one or more channels 40 is denoted by dashed line 44 in FIG. 7a. As air stream 44 flows through the one or more channels 40, aerosol precursor in the activation surface 38, across which the air stream 44 flows, is released from the activation surface 38 by heat conveyed to the activation surface from the heater 24. Aerosol precursor released from the activation surface 38 is entrained in air stream 44 flowing through the one or more channels 40. In use, the heater 24 of the apparatus 12 conveys heat to the fluid-transfer article 34 to raise a temperature of the activation surface 38 to a sufficient temperature to release, or liberate, captive substances (i.e. the aerosol precursor) held at the activation surface 38 of the fluid-transfer article 34 to form a vapour and/or aerosol, which is drawn downstream across the activation surface 38 of the fluid-transfer article. As the air stream 44 continues its passage in the one or more channels 40, more released aerosol precursor is entrained within the air stream 44. When the air stream 44 entrained with aerosol precursor exits the one or more channels 40 at a second side of the activation surface 38, it is directed to an outlet, from where it can be inhaled by the user via a mouthpiece. An outgoing air stream 46 entrained with aerosol precursor is directed to the outlet (e.g. via a fluid communication pathway within the housing of the carrier).

Therefore, operation of the apparatus will cause heat from the heater 24 to be conveyed to the activation surface 38 of the fluid-transfer article. At a sufficiently high temperature, captive substances held at the activation surface 38 of the fluid-transfer article are released, or liberated, to form a vapour and/or aerosol. Thus, when a user draws on a mouthpiece of the apparatus, the released substances from the fluid-transfer article are drawn away from the activation surface 38 (entrained in a stream of air) and condense to form an aerosol that is drawn through the a gas communication pathway for delivery to an outlet, which is in fluid communication with the mouthpiece.

As the aerosol precursor is released from the activation surface 38, a wicking effect of the fluid-transfer article 34 causes aerosol precursor within the body of the fluid-transfer article to migrate to the activation surface 38 to replace the aerosol precursor released from the activation surface 38 into air stream 44.

Operation of the heater 24 is controlled by control circuitry (not shown), which is operable to actuate the heater 24 responsive to an actuation signal from a switch operative by a user or configured to detect when the user draws air through a mouthpiece of the apparatus by sucking or inhaling. In an optional arrangement, the control circuitry operates to actuate the heater 24 with as little delay as possible from receipt of the actuation signal from the switch, or detection when the user draws air through the mouthpiece. This may effect instantaneous heating of the activation surface 38 of the fluid-transfer article 34.

In the illustrated example of use of the apparatus schematically illustrated in FIG. 7b, rather than the case of FIG. 7a, where air is drawn toward the activation surface 38 from one end only (and exits from the one or more channels 40 at an opposite end), a gas communication pathway for an incoming air stream is configured to deliver the incoming air stream to the activation surface from both ends. In such an arrangement, a gas communication pathway for an outlet airstream may be provided through the body of the fluid-transfer article 34. An outlet fluid communication pathway for an outlet airstream in the illustrative example of FIG. 7b is denoted by reference number 48.

Thus, in the illustrative example of FIG. 7b, when a user sucks on a mouthpiece of the apparatus, air is drawn into the carrier through inlet apertures (not shown) provided in a housing of the carrier. An incoming air stream 42a from a first end is directed to a first end of the activation surface 38 of the fluid-transfer article 34 (e.g. via a gas communication pathway within the housing of the carrier). An incoming air stream 42b from a second end is directed to a second end of the activation surface 38 of the fluid-transfer article 34 (e.g. via a gas communication pathway within the housing of the carrier. When the incoming air stream 42a from the first end reaches the first end of the activation surface 38, the incoming air stream 42a from the first end flows across the activation surface 38 via the one or more channels 40 formed between the activation surface 38 and the conduction element 36 (or between the activation surface 38 and heater 24). Likewise, when the incoming air stream 42b from the second end reaches the second end of the activation surface 38, the incoming air stream 42b from the second end flows across the activation surface 38 via the one or more channels 40 formed between the activation surface 38 and the conduction element 36 (or between the activation surface 38 and heater 24). The air streams from each end flowing through the one or more channels 40 are denoted by dashed lines 44a and 44b in FIG. 7a. As air streams 44a and 44b flow through the one or more channels 40, aerosol precursor in the activation surface 38, across which the air streams 44a and 44b flow, is released from the activation surface 38 by heat conveyed to the activation surface from the heater 24. Aerosol precursor released from the activation surface 38 is entrained in air streams 44a and 44b flowing through the one or more channels 40. In use, the heater 24 of the apparatus 12 conveys heat to the fluid-transfer article 34 to raise a temperature of the activation surface 38 to a sufficient temperature to release, or liberate, captive substances (i.e. the aerosol precursor) held at the activation surface 38 of the fluid-transfer article 34 to form a vapour and/or aerosol, which is drawn downstream across the activation surface 38 of the fluid-transfer article. As the air streams 44a and 44b continue their passages in the one or more channels 40, more released aerosol precursor is entrained within the air streams 44a and 44b. When the air streams 44a and 44b entrained with aerosol precursor meet at a mouth of the outlet fluid communication pathway 48, they enter the outlet fluid communication pathway 48 and continue until they exit outlet fluid communication pathway 48, either as a single outgoing air stream 46 (as shown), or as separate outgoing air streams. The outgoing air stream 46 is directed to an outlet, from where it can be inhaled by the user via a mouthpiece. The outgoing air stream 46 entrained with aerosol precursor is directed to the outlet (e.g. via a gas communication pathway within the housing of the carrier).

Figure 8A:
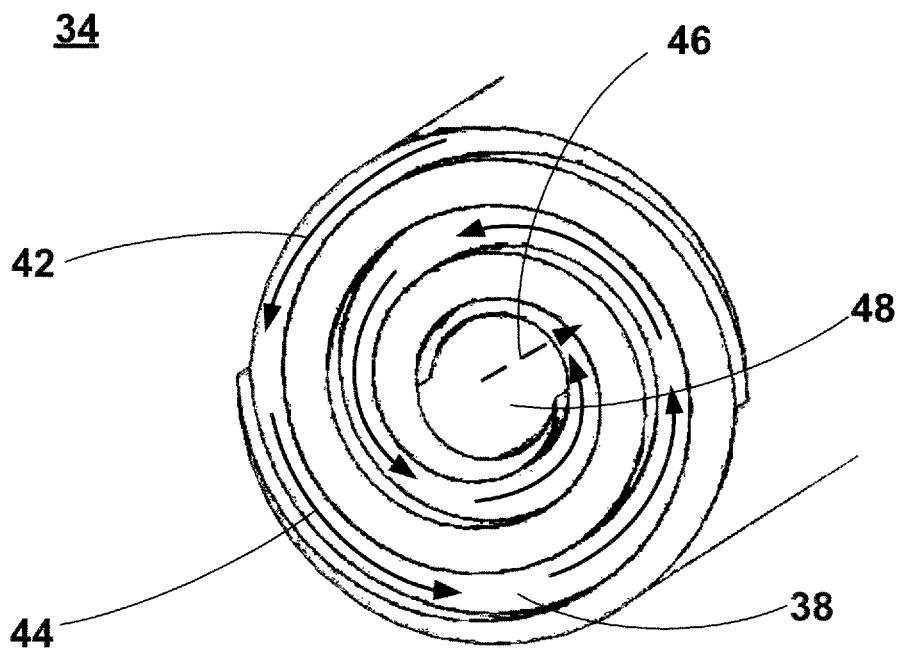
FIG. 8a is a perspective end view illustration of a fluid-transfer article of the aerosol carrier according to one or more embodiments of the present invention.
Figure 8B:
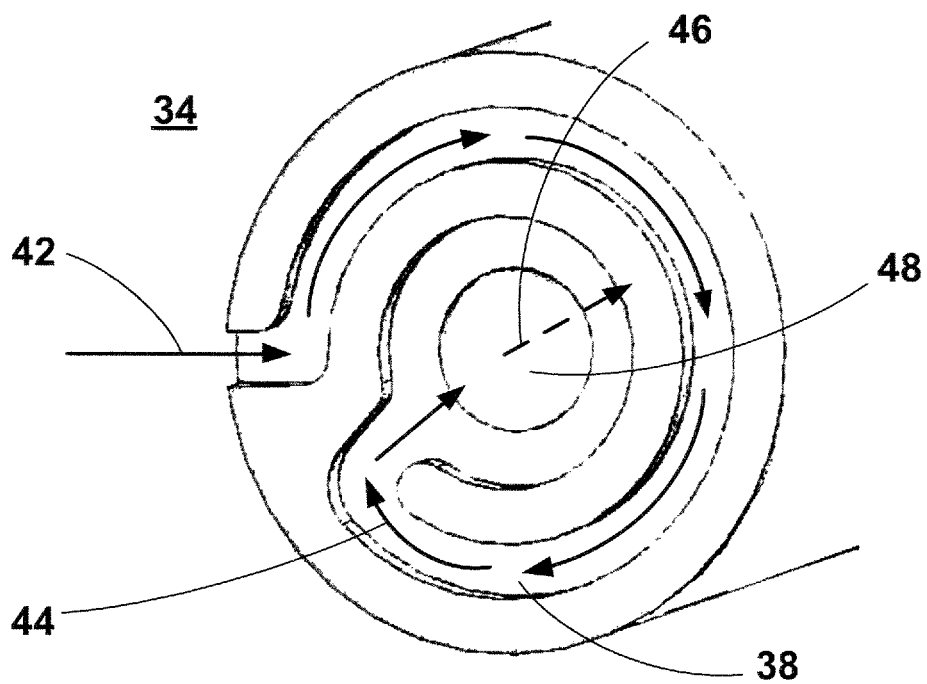
FIG. 8b is a perspective end view illustration of a fluid-transfer article of the aerosol carried according to one or more embodiments of the present invention.

FIGS. 8a and 8b are perspective end view illustrations of a fluid-transfer article 34 of the aerosol carrier according to one or more embodiments of the present invention. These figures show different types of channel configurations as illustrative examples. In both illustrative examples of a channel configuration, as shown in FIGS. 8a and 8b, the fluid-transfer article 34 comprises a cylindrical member, which comprises a central bore extending therethrough for fluid communication between the activation surface 38 and an outlet, from where an outgoing air stream can be delivered for inhalation. The central bore serves as a fluid communication pathway 48 (e.g. as described above in relation to FIG. 7b).

In both illustrative examples of FIGS. 8a and 8b, an incoming air stream 42 is directed to a mouth of a channel 40 formed between the activation surface 38 of the fluid-transfer article 34 and conduction element (not shown), or between the activation surface 38 and a heater (not shown). In both illustrative examples of FIGS. 8a and 8b, the mouth of the channel 40 is located at an outer edge of the fluid-transfer article 34 and an exit from the channel 40 (in fluid communication with the fluid communication pathway 48) is located toward a centre of the fluid-transfer article. Therefore, the incoming air stream 42 enters the channel 40 via channel mouth at the outer edge of the fluid-transfer article 34 and moves toward the centre of the fluid-transfer article 34 as directed by the channel 40. As described above, as the air stream passes across activation surface 38 through channel 40, aerosol precursor is released from the activation surface 38 and is entrained in air stream 44. Air stream 44 continues to flow through channel 40 until it reaches an exit thereof, from where it enters fluid communication pathway 48 and proceeds as an outgoing air stream 46 entrained with aerosol precursor toward the outlet.

In both illustrative examples of FIGS. 8a and 8b, the valleys or grooves of the activation surface 38 that form part of the channel 40 are arranged to define a circuitous route across the activation surface. In the illustrative examples, the route is a spiral path, but in optional arrangements, may be meandering or circuitous in some other manner. In optional arrangements, the activation surface may be located to face outwardly from the cylinder, such that the groove(s) or valley(s) may be in the outer surface of the cylinder forming the fluid-transfer article. These grooves or valleys may be arranged in parallel in a direction along the length of the cylinder. The groove(s) or valley(s) may be arranged in a spiral manner around the outside of the cylinder. In optional arrangements, the activation surface may be located to face inwardly from the cylinder (i.e. surrounding the central bore), such that the groove(s) or valley(s) may be in the inner surface of the cylinder forming the fluid-transfer article. These grooves or valleys may be arranged in parallel in a direction along the length of the cylinder. The groove(s) or valley(s) may be arranged in a spiral manner around the inside of the cylinder.

Figure 9A:
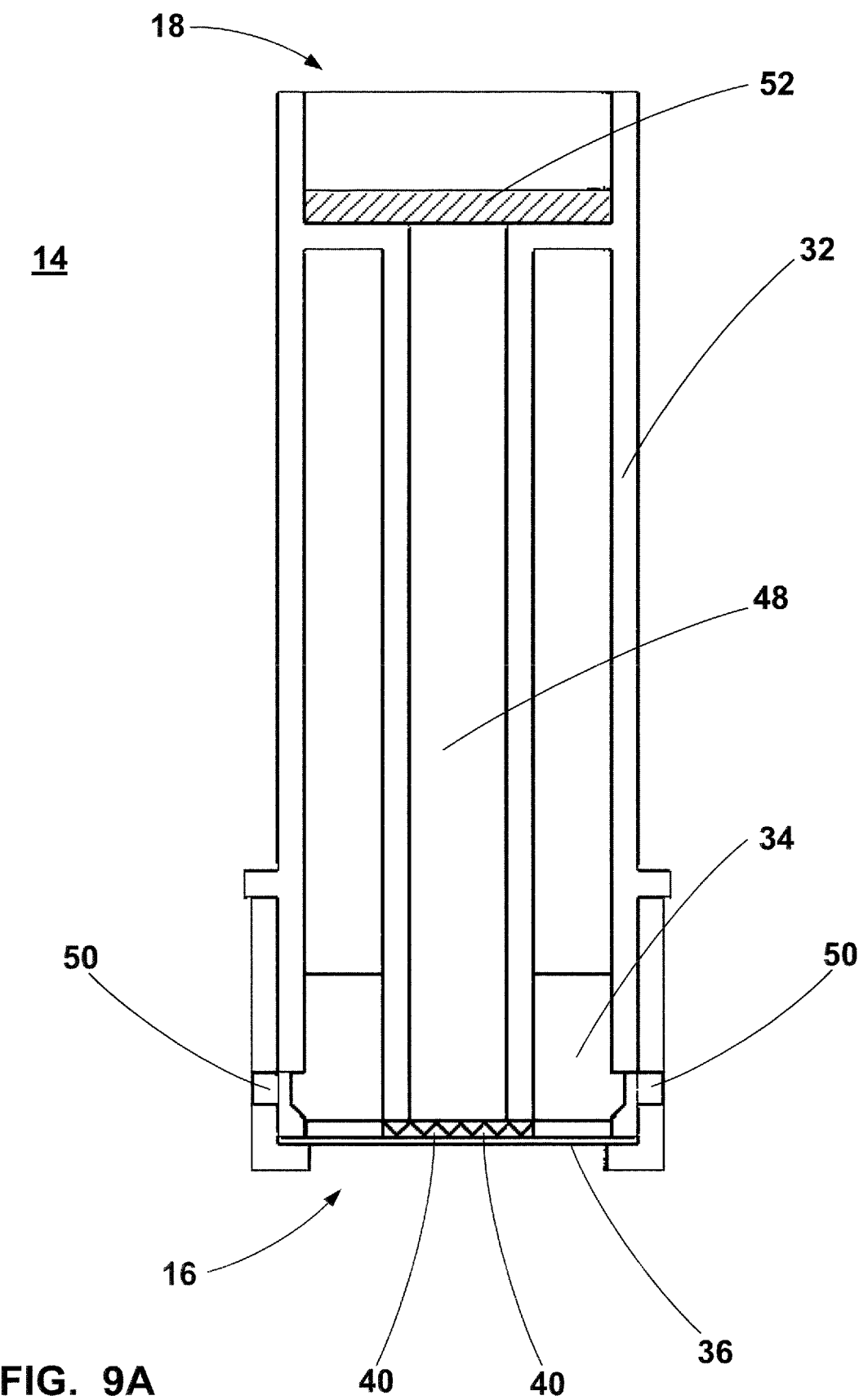
FIG. 9a is a cross-section side view of an aerosol carrier according to one or more embodiments of the present invention.
Figure 9B:
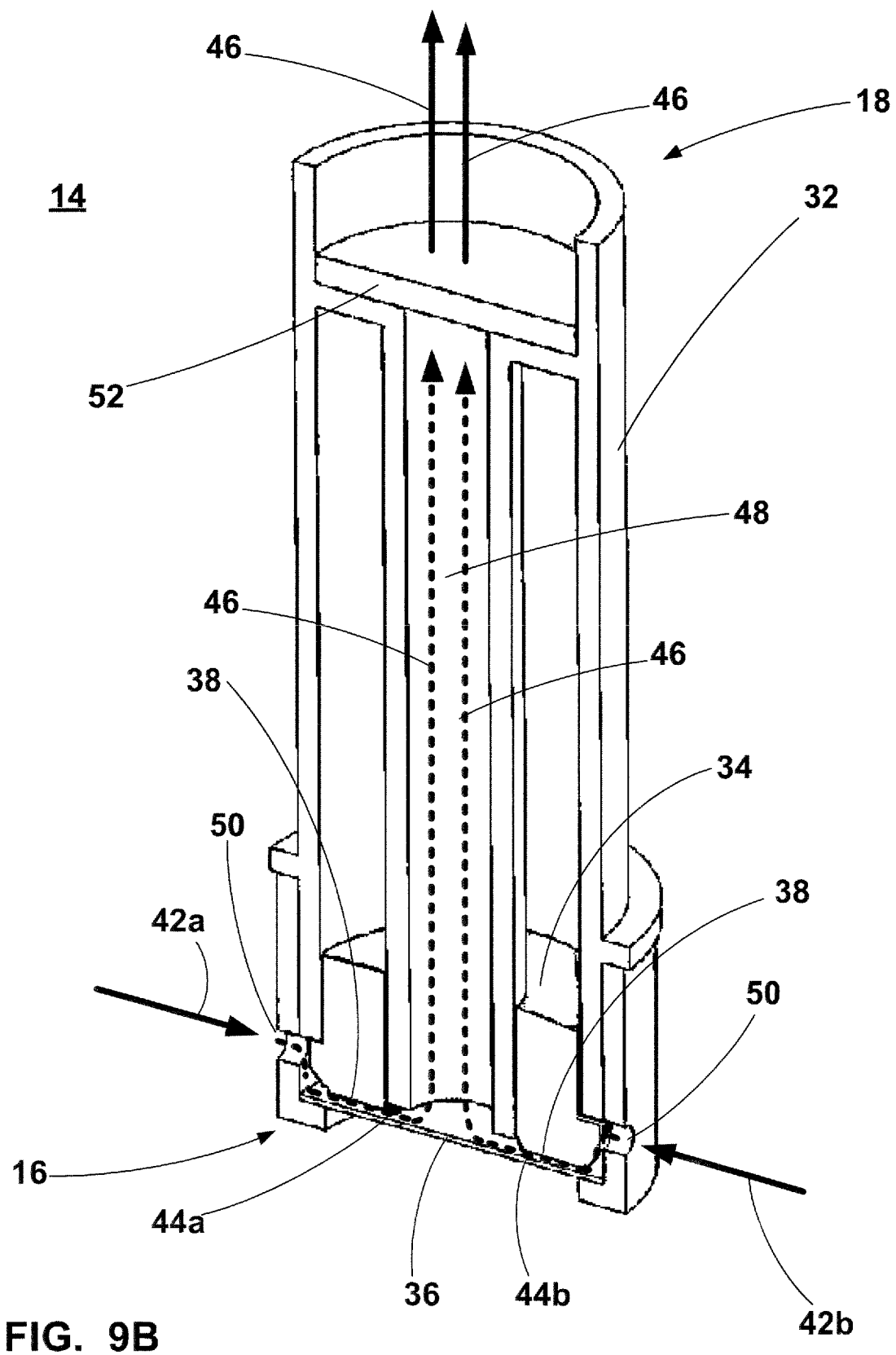

FIGS. 9a and 9b illustrate an aerosol carrier 14 according to one or more embodiments of the present invention in more detail. FIG. 9a is a cross-section side view illustration of the aerosol carrier 14 and FIG. 9b is a perspective cross-section side view illustration of the aerosol carrier 14 of FIG. 9a.

As can be seen from FIGS. 9a and 9b, the aerosol carrier 14 is generally tubular in form. The aerosol carrier 14 comprises housing 32, which defines the external walls of the aerosol carrier 14 and which defines therein a chamber in which are disposed the fluid-transfer article 34 (adjacent the first end 16 of the aerosol carrier 14) and internal walls defining the fluid communication pathway 48. Fluid communication pathway 48 defines a fluid pathway for an outgoing air stream from the channels 40 to the second end 18 of the aerosol carrier 14. In the examples illustrated in FIGS. 9a and 9b, the fluid-transfer article 34 is an annular shaped element located around the fluid communication pathway 48.

In walls of the housing 32, there are provided inlet apertures 50 to provide a fluid communication pathway for an incoming air stream to reach the fluid-transfer article 34, and particularly the one or more channels 40 defined between the activation surface of the fluid-transfer article 34 and the conduction element 36 (or between the activation surface and the heater).

In the illustrated example of FIGS. 9a and 9b, the aerosol carrier 14 further comprises a filter element 52. The filter element 52 is located across the fluid communication pathway 48 such that an outgoing air stream passing through the fluid communication pathway 48 passes through the filter element 52.

With reference to FIG. 9b, when a user sucks on a mouthpiece of the apparatus (or one the second end 18 of the aerosol carrier 14, if configured as a mouthpiece), air is drawn into the carrier through inlet apertures 50 extending through walls in the housing 32 of the aerosol carrier 14. An incoming air stream 42a from a first side of the aerosol carrier 14 is directed to a first side of the activation surface 38 of the fluid-transfer article 34 (e.g. via a gas communication pathway within the housing of the carrier). An incoming air stream 42b from a second side of the aerosol carrier 14 is directed to a second side of the activation surface 38 of the fluid-transfer article 34 (e.g. via a gas communication pathway within the housing of the carrier). When the incoming air stream 42a from the first side of the aerosol carrier 14 reaches the first side of the activation surface 38, the incoming air stream 42a from the first side of the aerosol carrier 14 flows across the activation surface 38 via the one or more channels 40 formed between the activation surface 38 and the conduction element 36 (or between the activation surface 38 and heater 24). Likewise, when the incoming air stream 42b from the second side of the aerosol carrier 14 reaches the second side of the activation surface 38, the incoming air stream 42b from the second side of the aerosol carrier 14 flows across the activation surface 38 via the one or more channels 40 formed between the activation surface 38 and the conduction element 36 (or between the activation surface 38 and heater 24). The air streams from each side flowing through the one or more channels 40 are denoted by dashed lines 44a and 44b in FIG. 9b. As air streams 44a and 44b flow through the one or more channels 40, aerosol precursor in the activation surface 38, across which the air streams 44a and 44b flow, is released from the activation surface 38 by heat conveyed to the activation surface from the heater 24. Aerosol precursor released from the activation surface 38 is entrained in air streams 44a and 44b flowing through the one or more channels 40. In use, the heater 24 of the apparatus 12 conveys heat to the activation surface 38 of the fluid-transfer article 34 to raise a temperature of the activation surface 38 to a sufficient temperature to release, or liberate, captive substances (i.e. the aerosol precursor) held at the activation surface 38 of the fluid-transfer article 34 to form a vapour and/or aerosol, which is drawn downstream across the activation surface 38 of the fluid-transfer article 34. As the air streams 44a and 44b continue their passages in the one or more channels 40, more released aerosol precursor is entrained within the air streams 44a and 44b. When the air streams 44a and 44b entrained with aerosol precursor meet at a mouth of the outlet fluid communication pathway 48, they enter the outlet fluid communication pathway 48 and continue until they pass through filter element 52 and exit outlet fluid communication pathway 48, either as a single outgoing air stream, or as separate outgoing air streams 46 (as shown). The outgoing air streams 46 are directed to an outlet, from where it can be inhaled by the user directly (if the second end 18 of the aerosol capsule 14 is configured as a mouthpiece), or via a mouthpiece. The outgoing air streams 46 entrained with aerosol precursor are directed to the outlet (e.g. via a gas communication pathway within the housing of the carrier).

When the user initially sucks on a mouthpiece of the apparatus (or one the second end 18 of the aerosol carrier 14, if configured as a mouthpiece), this will cause an air column located in the fluid communication pathway 48 to move towards the outlet. In turn, this will draw air into the fluid communication pathway from the one or more channels 40. This will cause a pressure drop in the channels 40. To equalise the pressure in the channels 40, air will be drawn into the aerosol carrier 14, and thus into the channels 40 via the inlet aperture 50. During the period of lower pressure in the one or more channels 40 when the user begins to suck, aerosol precursor in the fluid-transfer medium will be released into the channels from the activation surface 38, because the aerosol precursor is drawn into the one or more channels by way of the lower pressure. This effect is in addition to the effect of releasing the aerosol precursor from the activation surface 38 by way of heat conveyed from the heater.

The drawing of the aerosol precursor from the activation surface 38 by way of the user sucking on the mouthpiece of the apparatus (or one the second end 18 of the aerosol carrier 14, if configured as a mouthpiece) may produce a dragging effect on the volumetric rate of flow experienced by the user during a suction action, i.e. the user may have to suck harder to achieve a same volumetric rate of flow. This effect may manifest itself as a similar physical sensation experienced by the user as those experienced from a traditional smoking or tobacco product.

Figure 10:
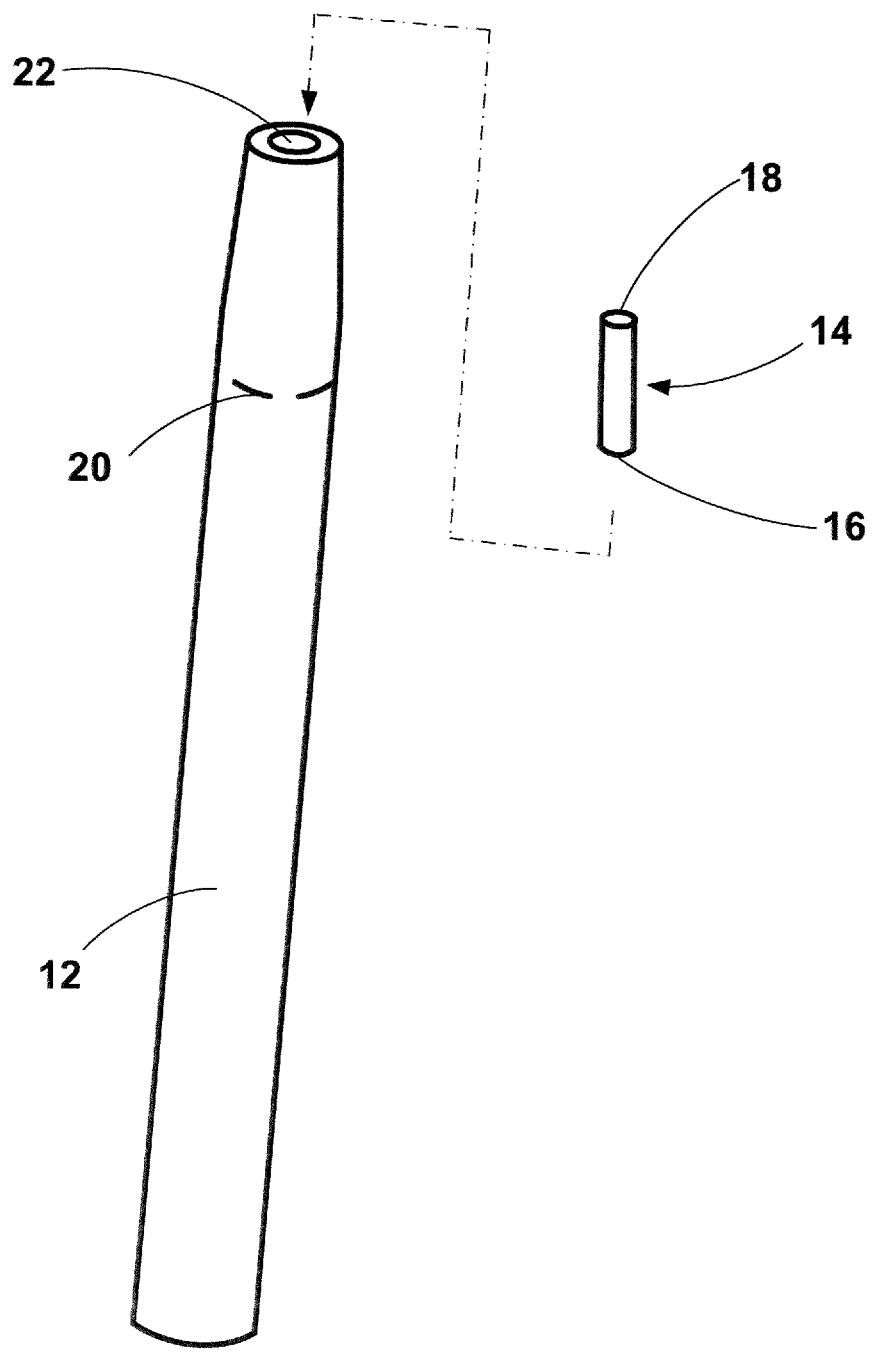
FIG. 10 is an exploded perspective view illustration of a kit-of-parts for assembling a system according to one or more embodiments of the present invention.

FIG. 10 is an exploded perspective view illustration of a kit-of-parts for assembling an aerosol delivery system 10 according to one or more embodiments of the present invention.

There has been described in the foregoing one or more embodiments of an aerosol delivery system that avoids or at least ameliorates the problems of the prior art.

In one or more optional arrangements, a fluid-transfer article 34 containing nicotine and/or nicotine compounds may be substituted or supplemented with a fluid-transfer article configured to provide a flavoured vapour and/or aerosol upon heating of the fluid-transfer article by the heater 24 of the apparatus 12. A precursor material for forming the flavoured vapour and/or aerosol upon heating is held within pores, spaces, channels and/or conduits within the fluid-transfer article. The precursor material may be extracted from a tobacco plant starting material using a supercritical fluid extraction process. Optionally, the precursor material is nicotine-free and comprises tobacco-flavours extracted from the tobacco plant starting material. Further optionally, the extracted nicotine-free precursor material (e.g. flavours only) could have nicotine added thereto prior to loading of the precursor material into the substrate of the carrier unit. Further optionally, flavours and physiologically active material may be extracted from plants other than tobacco plants.

As used herein any reference to "one embodiment" or "an embodiment" means that a particular element, feature, structure, or characteristic described in connection with the embodiment is included in at least one embodiment. Any appearances of the phrase "in one embodiment" or the phrase "in an embodiment" in the specification are not necessarily all referring to the same embodiment.

As used herein, the terms "comprises,", "comprising,", "includes,", "including,", "has,", "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

The scope of the present disclosure includes any novel feature or combination of features disclosed therein either explicitly or implicitly or any generalization thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. A fluid-transfer article comprising
a first region for holding an aerosol precursor and for transferring said aerosol precursor to an activation surface of a second region of said article, said activation surface disposed at an end of said article configured for thermal interaction with a heater of an aerosol-generation apparatus;
wherein said second region comprises at least one discontinuity in said activation surface to form a corresponding at least one channel between said activation surface and an opposing surface through which heat is conveyable to said activation surface from the heater, said at least one channel configured for providing a fluid pathway across said activation surface, said fluid pathway across said activation surface forming a portion of said fluid pathway between said first end and said second end.

2. The article according to claim 1, wherein said article comprises a tubular member.

3. The article according to claim 2, wherein said article comprises a bore extending therethrough, said first region extending axially along an external surface of said article and said second surface, located between said first region and said bore, extending axially along an internal surface of said article, said at least one discontinuity extending axially along said internal surface of said article formed by said bore.

4. The article according to claim 2, wherein said article comprises a bore extending therethrough, said first region extending axially along an internal surface of said article and said second surface extending axially along an external surface of said article, said at least one discontinuity extending axially at least partially along said external surface of said article.

5. The article according to claim 2, wherein an end surface of said tubular member comprises said activation surface and further wherein said at least one discontinuity extends radially across said activation surface.

6. The article according to claim 2, wherein an end surface of said tubular member comprises said activation surface and further wherein said at least one discontinuity extends linearly across said activation surface.

7. The article according to claim 2, wherein an end surface of said tubular member comprises said activation surface and further wherein said at least one discontinuity is serpentine across said activation surface.

8. The article according to claim 1, wherein said activation surface is formed at an interface between regions adjacent said at least one discontinuity and said opposing surface through which heat is conveyed to said activation surface from a heater.

9. The article according to claim 1, wherein a thermally conductive barrier layer is provided as said opposing surface through which heat is conveyable to said activation surface, said thermally conductive barrier layer configured for thermal contact with a heater and locatable between a heater and said activation surface of said article.

10. The article according to claim 9, where said activation surface and said opposing surface through which heat is conveyable to said activation surface are complementary.

11. The article according to claim 1, wherein said article is formed of a thermally conductive material.

12. The article according to claim 1, wherein said article is formed of a plastic material.

13. The article according to claim 1, wherein said article is formed from a hydrophilic material that is configured to transfer fluid from said first region to said second region.

14. The article according to claim 1, wherein said article is formed from a sintered material.

15. The article according to claim 1, wherein said article comprises a plurality of regions having different structures.

16. The article according to claim 1, wherein said article is formed of a porous material in which pore diameter in said first region is greater than pore diameter in said second region.

17. The article according to claim 1, wherein said article is formed of a material that is of greater hydrophilicity in said second region than said first region.

18. The article according to claim 1, wherein said article is formed of a wicking material comprising a graduated wicking action.

19. A carrier for an aerosol precursor comprising:
a housing for location in a receptacle of an aerosol-generating apparatus, said housing configured to provide a fluid pathway between a first end that is disposed in fluid engagement with an inlet of said aerosol-generating apparatus and a second end that is disposed in fluid engagement with an outlet of said aerosol-generating apparatus; and
a fluid-transfer article according to claim 1 located within said housing, said activation surface being disposed at an end of said carrier configured for thermal interaction with a heater of an aerosol-generation apparatus.

20. An aerosol-delivery system comprising:
an aerosol-generation apparatus comprising:
a receptacle for receiving a carrier; a heater;
and a carrier according to claim 19, wherein:
said housing is for location in said receptacle; and
said activation surface is disposed at an end of said carrier configured for thermal interaction with said heater of said aerosol-generation apparatus.

21. The system according to claim 20, wherein said heater comprises a planar heating surface.

22. The system according to claim 20, wherein said heater is a rod extending axially through said centre of said fluid transfer article.

23. The system according to claim 20, wherein said heater comprises a collar arranged around said article.

24. The system according to claim 23, wherein said collar extends over a length of said article.

25. The system according to claim 24, wherein said collar extends over said second region of said article.

26. The system according to claim 20, wherein said heater comprises said opposing surface through which heat is conveyed to said activation surface, said heater in contact with said activation surface of said article.

27. A kit-of-parts for assembling a system for aerosol delivery, comprising: an aerosol-generation apparatus comprising:
a receptacle for receiving a carrier;
a heater;
a carrier for an aerosol precursor, said carrier locatable in said receptacle, and said carrier comprising:
a housing for location in said receptacle, said housing configured to provide a fluid pathway between a first end that is disposed in fluid engagement with an inlet of said aerosol-generating apparatus and a second end that is disposed in fluid engagement with an outlet of said aerosol-generation apparatus; and
a fluid-transfer article located within said housing, said fluid-transfer article comprising a first region for holding an aerosol precursor and for transferring said aerosol precursor to an activation surface of a second region of said article, said activation surface disposed at an end of said carrier configured for thermal interaction with a heater of said aerosol-generation apparatus;
wherein said second region comprises at least one discontinuity in said activation surface to form a corresponding at least one channel between said activation surface and an opposing surface through which heat is conveyable to said activation surface from said heater, said at least one channel configured for providing a fluid pathway across said activation surface, said fluid pathway across said activation surface forming a portion of said fluid pathway between said first end and said second end.

* * * * *